(12) United States Patent
Stupp et al.

(10) Patent No.: US 8,748,569 B2
(45) Date of Patent: Jun. 10, 2014

(54) PEPTIDE AMPHIPHILES AND METHODS TO ELECTROSTATICALLY CONTROL BIOACTIVITY OF THE IKVAV PEPTIDE EPITOPE

(75) Inventors: Samuel I. Stupp, Chicago, IL (US); Joshua E. Goldberger, Columbus, OH (US); Eric J. Berns, Chicago, IL (US)

(73) Assignee: Northwestern University, Evanston, IL (US)

( * ) Notice: Subject to any disclaimer, the term of this patent is extended or adjusted under 35 U.S.C. 154(b) by 0 days.

(21) Appl. No.: 13/442,210

(22) Filed: Apr. 9, 2012

(65) Prior Publication Data
US 2012/0294902 A1 Nov. 22, 2012

Related U.S. Application Data

(60) Provisional application No. 61/473,593, filed on Apr. 8, 2011.

(51) Int. Cl.
| | |
|---|---|
| A61K 38/02 | (2006.01) |
| C07K 2/00 | (2006.01) |
| A61K 38/00 | (2006.01) |
| A61K 9/51 | (2006.01) |
| B82Y 5/00 | (2011.01) |

(52) U.S. Cl.
CPC . A61K 38/00 (2013.01); C07K 2/00 (2013.01); C07K 2319/735 (2013.01); A61K 9/5169 (2013.01); B82Y 5/00 (2013.01); Y10S 977/795 (2013.01)
USPC .................. 530/300; 530/345; 977/795

(58) Field of Classification Search
CPC ... A61K 38/00; A61K 9/0019; A61K 9/0024; A61K 9/5169; C07K 14/78; C07K 2319/735; C07K 2/00; B82Y 5/00
See application file for complete search history.

(56) References Cited

U.S. PATENT DOCUMENTS

2006/0247165 A1 11/2006 Stupp et al.

OTHER PUBLICATIONS

Cui et al, Spontaneous and X-ray—Triggered Crystallization at Long Range in Self-Assembling Filament Networks, Science, 2010, 327, pp. 555-559.*
Cui et al, Spontaneous and X-ray—Triggered Crystallization at Long Range in Self-Assembling Filament Networks, Science, 2010, 327, supporting materials, pp. 1-47.*
Angeloni et al, Regeneration of the cavernous nerve by Sonic hedgehog using aligned peptide amphiphile nanofibers, Biomaterials, 2011, 32, pp. 1091-1101.*
Rudinger, Peptide Hormones, JA Parsons, Ed., 1976, pp. 1-7.*
SIGMA, 2004, pp. 1-2.*
Berendsen, A Glimpae of the Holy Grail?, Science, 1998, 282, pp. 642-643.*
Voet et al, Biochemistry, John Wiley & Sons Inc., 1995, pp. 235-241.*
Ngo et al, Computational Complexity, Protein Structure Protection, and the Levinthal Paradox, 1994, pp. 491-494.*
Bradley et al., Limits of Cooperativity in a Structurally Modular Protein: Response of the Notch Ankyrin Domain to Analogous Alanine Substitutions in Each Repeat, J. Mol. BIoL (2002) 324, 373-386.*
Tysseling et al., "Self-assembling peptide amphiphile promotes plasticity of serotonergic fibers following spinal cord injury," J Neurosci Res, 2010, 88: 3161-3170.
Tysseling-Mattiace et al., "Self-assembling nanofibers inhibit glial scar formation and promote axon elongation after spinal cord injury," J Neurosci, 2008, 28: 3814-3823.
Wheeler et al., "Microcontact printing for precise control of nerve cell growth in culture," J Biomech Eng, 1999, 121: 73-78.
Yamada et al., "Ile-Lys-Val-Ala-Val (IKVAV)-containing laminin alpha1 chain peptides form amyloid-like fibrils," FEBS Lett, 2002, 530: 48-52.
Yeung et al., "Modulation of the growth and guidance of rat brain stem neurons using patterned extracellular matrix proteins," Neurosci Lett, 2001, 301: 147-150.
Yoshida et al., "Identification of a heparin binding site and the biological activities of the laminin alpha1 chain carboxy-terminal globular domain," J Cell Physiol, 1999, 179: 18-28.
Zhang et al., "Compatibility of neural stem cells with functionalized self-assembling peptide scaffold in vitro," Biotech Bioprocess Engineering, 2010, 15: 545-551.
Zou et al., "Growth of rat dorsal root ganglion neurons on a novel self-assembling scaffold containing IKVAV sequence," Mater Sci Engineering: C, 2009, 29(7)o: 2099-2103.
Zustiak et al., "Influence of cell-adhesive peptide ligands on poly-(ethylene glycol) hydrogel physical, mechanical and transport properties," Acta Biomater, 2010, 6: 3404-3414.
Adams et al., "Growth cones turn and migrate up an immobilized gradient of the laminin IKVAV peptide," J Neurobiol, 2005, 62:134-147.
Agheli et al., "Large area protein nanopatterning for biological applications," Nano Lett, 2006, 6: 1165-1171.
Agius et al., "Antibodies directed against the beta 1-integrin subunit and peptides containing the IKVAV sequence of laminin perturb neurite outgrowth of peripheral neurons on immature spinal cord substrata," Neurosci, 1996, 71:773-786.

(Continued)

Primary Examiner — Julie Ha
Assistant Examiner — Li Ni Komatsu
(74) Attorney, Agent, or Firm — Casimir Jones, S.C.

(57) ABSTRACT

The present invention is directed to peptide amphiphile compounds, compositions and methods of use, wherein nanofiber bundling or epitope aggregation is inhibited. In certain embodiments, the peptide amphiphiles of the present invention have increased solubility and reduced nanofiber bundling. The molecules may be used in pharmaceutical applications, for example for in vivo administration to human patients, by increasing biological activity of the compositions toward neurite outgrowth and nerve regeneration.

5 Claims, 17 Drawing Sheets

(56) References Cited

OTHER PUBLICATIONS

Bellamkonda et al., "Laminin oligopeptide derivatized agarose gels allow three-dimensional neurite extension in vitro," J Neurosci Res, 1995, 41:501-509.
Berat et al., "Peptide-presenting two-dimensional protein matrix on supported lipid bilayers: an efficient platform for cell adhesion," Biointerphases, 2007, 2: 165-172.
Chalazonitis et al., "The alpha1 subunit of laminin-1 promotes the development of neurons by interacting with LBP110 expressed by neural crest-derived cells immunoselected from the fetal mouse gut," J Neurobiol, 1997, 33: 118-138.
Chang et al., "Modulation of neural network activity by patterning," Biosens Bioelectron, 2001, 16(7-8): 527-533.
Cornish et al., "Microcontact printing: a versatile technique for the study of synaptogenic molecules," Mol Cell Neurosci, 2002, 20: 140-153.
Cui et al., "Cerebrum Repair with PHPMA Hydrogel Immobilized with Neurite-Promoting Peptides in Traumatic Brain Injury of Adult Rat Model," J Bioactive and Compatible Polymers, 2003, 18: 413-432.
Duque et al., "Immobilization of biomolecules to plasma polymerized pentafluorophenyl methacrylate," Biomacromolecules, 2010 11: 2818-2823.
Ehteshami et al., "Immobilization of bioactive peptides on benzocyclobutene (BCB) surface grafted-dextran for neural implant applications," Proceedings of the 25th Annual International Conference IEEE Engineering Med Biol Soc, 2003, 1-4, 25: 2180-2181.
Heller et al., "Patterned networks of mouse hippocampal neurons on peptide-coated gold surfaces," Biomaterials, 2005, 26: 883-889.
Hynd et al., "Directed cell growth on protein-functionalized hydrogel surfaces," J Neurosci Methods, 2007, 162: 255-263.
Itoh et al., "Development of a nerve scaffold using a tendon chitosan tube," Artif Organs, 2003, 27: 1079-1088.
Jung et al., "Selective and direct immobilization of cysteinyl biomolecules by electrochemical cleavage of azo linkage," Langmuir, 2010, 26: 15087-15091.
Jung et al., "Co-assembling peptides as defined matrices for endothelial cells," Biomaterials, 2009, 30: 2400-2410.
Kam et al., "Axonal outgrowth of hippocampal neurons on microscale networks of polylysine-conjugated laminin," Biomaterials, 2001, 22: 1049-1054.
Kasai et al., "Identification of multiple amyloidogenic sequences in laminin-1," Biochemistry, 2007, 46: 3966-3974.
Kibbey et al., "A 110-kD nuclear shuttling protein, nucleolin, binds to the neurite-promoting IKVAV site of laminin-1," J Neurosci Res, 1995, 42: 314-322.
Kibbey et al., "beta-Amyloid precursor protein binds to the neurite-promoting IKVAV site of laminin," Proc Natl Acad Sci USA, 1993, 90: 10150-10153.
Kumada et al., "Functionalized scaffolds of shorter self-assembling peptides containing MMP-2 cleavable motif promote fibroblast proliferation and significantly accelerate 3-D cell migration independent of scaffold stiffness," Soft Matter, 2010, 6: 5073-5079.
Lauer et al., "Electrophysiological recordings of patterned rat brain stem slice neurons," Biomaterials, 2002, 23: 3123-3130.
Li et al., "Neural differentiation directed by self-assembling peptide scaffolds presenting laminin-derived epitopes," J Biomed Mater Res A, 2010, 94:688-699.
Luckenbill-Edds et al., "Localization of the 110 kDa receptor for laminin in brains of embryonic and postnatal mice," Cell Tiss Res, 1995, 279: 371-377.
Massia et al., "In vitro assessment of bioactive coatings for neural implant applications," J Biomed Mater Res A, 2004, 68: 177-186.
Matsuzawa et al., "Directional neurite outgrowth and axonal differentiation of embryonic hippocampal neurons are promoted by a neurite outgrowth domain of the B2-chain of laminin," Int J Dev Neurosci, 1996, 14: 283-295.
Nakamura et al., "Construction of a multi-functional extracellular matrix protein that increases number of N1E-115 neuroblast cells having neurites," J Biomed Mater Res B Appl Biomater, 2009, 91:425-432.
Niece et al., "Modification of gelation kinetics in bioactive peptide amphiphiles," Biomaterials, 2008, 4501-4509.
Nomizu et al., "[Identification of biologically active sites in laminin an extracellular matrix protein]," Yakugak Zasshi : J Pharm Society Japan, 1998, 118: 566-580, with English Abstract.
Nomizu et al., "Identification of cell binding sites in the laminin alpha 1 chain carboxyl-terminal globular domain by systematic screening of synthetic peptides," J Biol Chem, 1995, 270: 20583-20590.
Nomizu et al., "Cell binding sequences in mouse laminin alpha1 chain," J Biol Chem, 1998, 273: 32491-32499.
Nomizu et al., "The all-D-configuration segment containing the IKVAV sequence of laminin A chain has similar activities to the all-L-peptide in vitro and in vivo," J Biol Chem, 1992, 267: 14118-14121.
Nomizu et al., "Structure-activity study of a laminin alpha 1 chain active peptide segment Ile-Lys-Val-Ala-Val (IKVAV)," FEBS Lett, 1995, 365: 227-231.
Ohga et al., "Design and activity of multifunctional fibrils using receptor-specific small peptides," Biomaterials, 2009, 30:6731-6738.
Patel et al., "Spatially controlled cell engineering on biodegradable polymer surfaces," FASEB Journal, 1998, 12: 1447-1454.
Powell et al., "Neural cell response to multiple novel sites on laminin-1," J Neurosci Res, 2000, 61: 302-312.
Ranieri et al., "Spatial control of neuronal cell attachment and differentiation on covalently patterned laminin oligopeptide substrates," Int J DevNeurosci, 1994, 12: 725-735.
Ranieri et al., "Neuronal cell attachment to fluorinated ethylene propylene films with covalently immobilized laminin oligopeptides YIGSR and IKVAV. II," J Biomed Mater Res, 1995, 29: 779-785.
Richard et al., "Identification of synthetic peptides derived from laminin alpha1 and alpha2 chains with cell type specificity for neurite outgrowth," Exp Cell Res, 1996, 228: 98-105.
Saha et al., "Biomimetic interfacial interpenetrating polymer networks control neural stem cell behavior," J Biomed Mater Res A, 2007, 81: 240-249.
Saneinejad et al., "Patterned glass surfaces direct cell adhesion and process outgrowth of primary neurons of the central nervous system," J Biomed Mater Res, 1998, 42:13-19.
Santiago et al., "Peptide-surface modification of poly(caprolactone) with laminin-derived sequences for adipose-derived stem cell applications," Biomaterials, 2006, 27: 2962-2969.
Shaw et al., "Toward spinal cord injury repair strategies: peptide surface modification of expanded poly (tetrafluoroethylene) fibers for guided neurite outgrowth in vitro," J Craniofacial Surg, 2003, 14: 308-316.
Silva et al., "Selective differentiation of neural progenitor cells by high-epitope density nanofibers," Science, 2004, 303: 1352-1355.
Song et al., "Two-dimensional effects of hydrogel self-organized from IKVAV-containing peptides on growth and differentiation of NSCs," J Wuhan Univ Tech Mater Sci Ed, 2009, 24: 186-192.
Svedhem et al., "In situ peptide-modified supported lipid bilayers for controlled cell attachment," Langmuir, 2003, 19: 6730-6736.
Tong et al., "Enhancing the neuronal interaction on fluoropolymer surfaces with mixed peptides or spacer group linkers," Biomaterials, 2001, 22: 1029-1034.
Takagi et al., "Conserved neuron promoting activity in Drosophila and vertebrate laminin alpha1," J Biol Chem, 1996, 271: 18074-18081.
Tashiro et al., "A synthetic peptide deduced from the sequence in the cross-region of laminin A chain mediates neurite outgrowth, cell attachment and heparin binding," Biochem J, 1994, 302: 73-79.
Tashiro et al., "A synthetic peptide containing the IKVAV sequence from the A chain of laminin mediates cell attachment, migration, and neurite outgrowth," J Biol Chem, 1989, 264: 16174-16182.

* cited by examiner

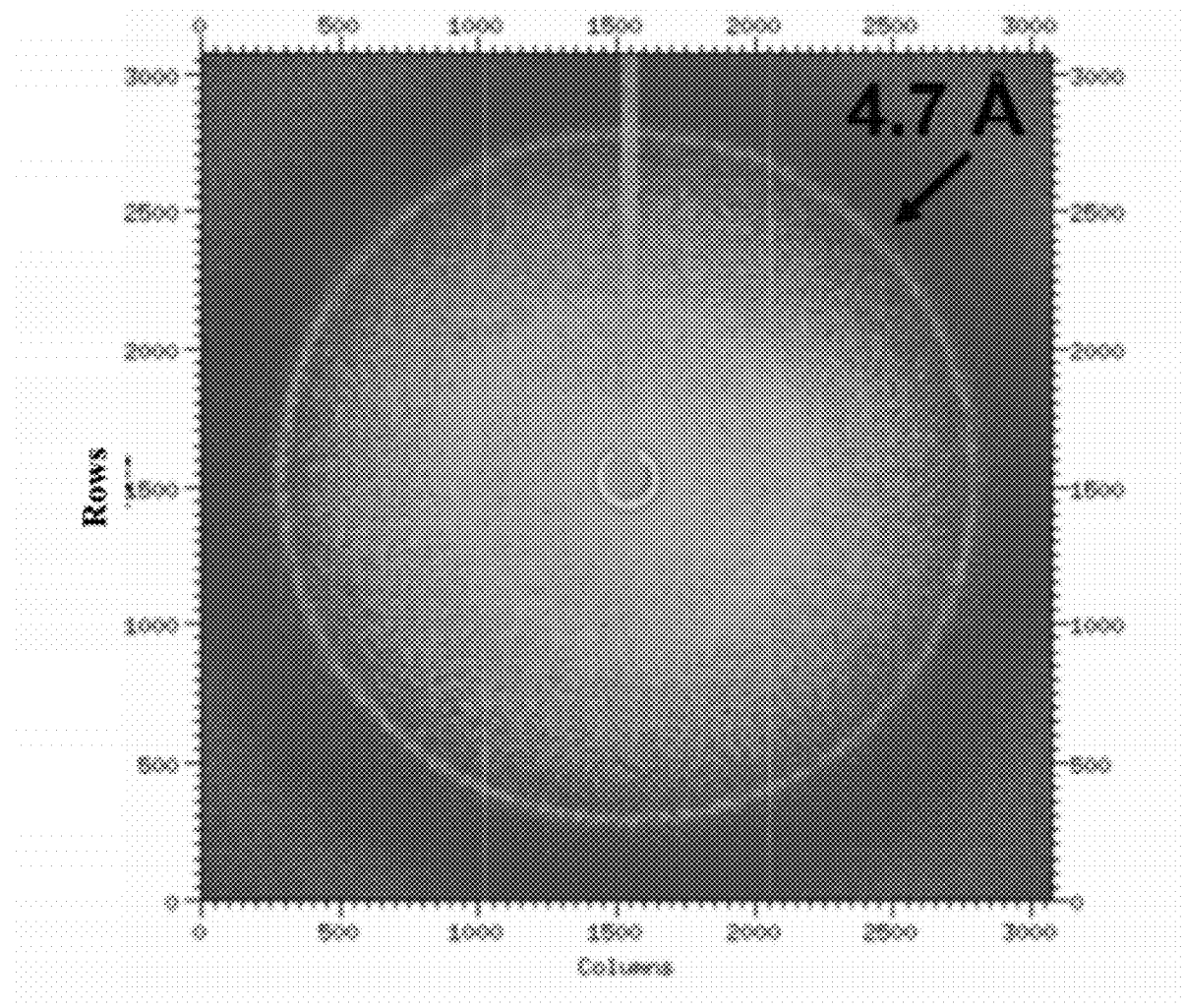

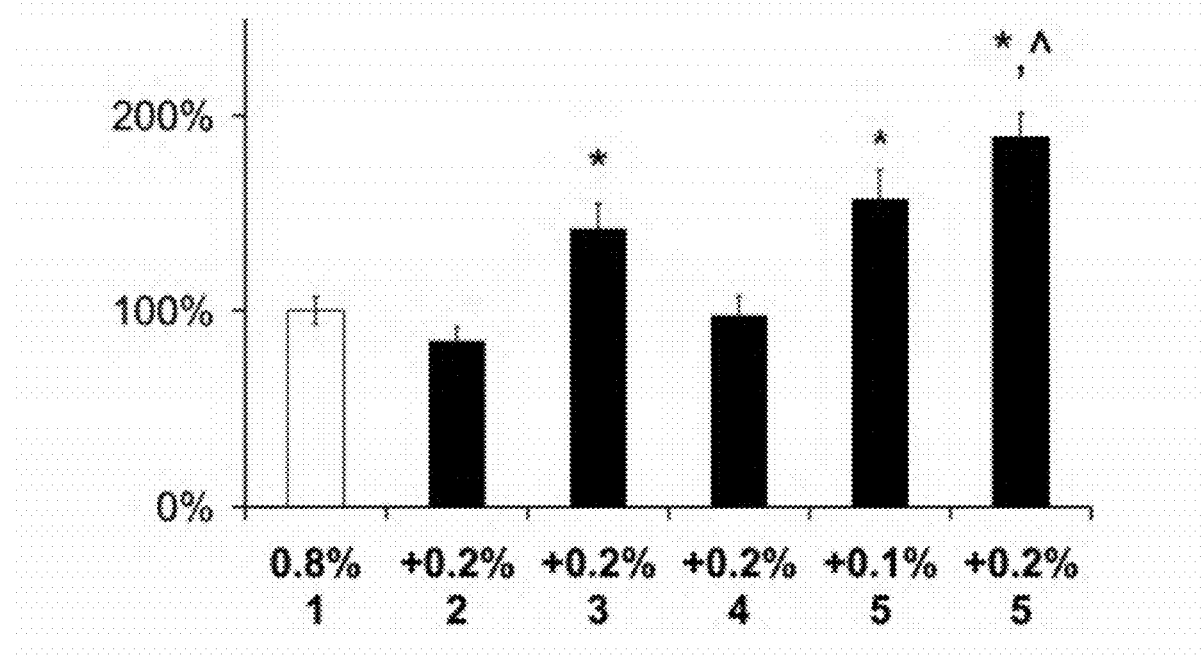

PEPTIDE AMPHIPHILES AND METHODS TO ELECTROSTATICALLY CONTROL BIOACTIVITY OF THE IKVAV PEPTIDE EPITOPE

STATEMENT REGARDING FEDERAL FUNDING

This invention was made with government support under grants number R01 EB003806 and 5 F32 EB007131 awarded by the National Institutes of Health and contract number W911NF-09-1-0044 awarded by the Department of Defense through the Defense Advanced Research Projects Agency (DARPA). The government has certain rights in this invention.

CROSS-REFERENCE TO RELATED APPLICATIONS

The present invention claims the benefit of U.S. Provisional Patent Application Ser. No. 61/473,593, filed Apr. 8, 2011, which is incorporated by reference in its entirety.

FIELD OF THE INVENTION

The present invention relates generally to improved peptide amphiphiles (PAs) bearing the IKVAV (SEQ ID NO. 1) peptide sequence, peptide-amphiphile nanofibers and other nanostructures self-assembled therefrom and methods of making and using same. In certain embodiments, the present invention relates to peptide amphiphiles incorporating three or more ionizable side-chains disposed in such a manner as to modulate interfiber interdigitation of an IKVAV (SEQ ID NO. 1) epitope, or to promote surface presentation and biological availability of the IKVAV (SEQ ID NO. 1) epitope, upon self-assembly of the peptide amphiphile into aggregated structures. In certain embodiments, the present invention provides molecular designs of IKVAV (SEQ ID NO. 1) peptide amphiphiles that demonstrate greater ease of synthesis and purification, are more soluble in salt solutions resembling extracellular fluid, and exhibit surprisingly enhanced biological activity, including the promotion of neurite outgrowth, as compared with previously reported compounds. In certain embodiments, the peptide amphiphiles are used therapeutically (e.g., to treat injuries or diseases of the central nervous system (CNS), including spinal cord injury (SCI)).

BACKGROUND OF THE INVENTION

Designing artificial extracellular matrices that effectively signal and direct cellular responses is essential for the creation of new regenerative medicine therapies. However, the preparation of any synthetic material with structure on the nanoscale that mimics natural tissue is a challenging problem. One approach has been to prepare molecules that spontaneously assemble into fibers similar in morphology to the proteins and proteoglycans that compose the natural extracellular matrix. In contrast to most synthetic biopolymers, the use of small, self-assembling molecules facilitates control of chemical and structural properties of these macromolecular assemblies. Injectable, self-assembling biomaterials capable of forming scaffolds in situ around cells are promising therapeutic candidates because of their minimally invasive delivery. The signaling efficiency of self-assembling bioactive structures depends not only on molecular structure but also on nanoscale morphology. To that end, peptide amphiphiles have been shown to self-assemble under suitable conditions to form nanoscale aggregates having particular utility as biocompatible scaffolds, more particularly in the area of tissue engineering and regenerative medicine.

Peptide amphiphiles (PAs) constitute a class of molecules that spontaneously self-assemble into a variety of nanostructures, including spherical micelles, cylindrical fibers and ribbons, and have shown promising therapeutic activity. PA molecules that form cylindrical fiber-like nanostructures (termed in the art "nanofibers") have been found to be particularly useful in mimicking the biomechanical properties of the extracellular matrix. These PA molecules are composed typically of four main segments: (1) a hydrophobic moiety, commonly an acyl group derived from a fatty acid, that promotes molecular aggregation through hydrophobic collapse; (2) a β-sheet-forming peptide that promotes fiber assembly; (3) a peptide segment that contains ionizable side-chain residues; and (4) a peptide signaling moiety designed to interact with cellular receptors. These molecules self-assemble into high-aspect ratio nanostructures, forming gels in water at low concentrations when the charges on the ionic side chains are appropriately screened. Individual cylindrical nanofibers display bioactive sequences on their surface in high density. However, aggregation of nanofibers into bundles reduces the surface area for bioactive epitope presentation. Moreover, some PA molecules have proven difficult to synthesize and/or purify on a large scale. This can be due to the molecules' zwitterionic nature (i.e., carrying both positive and negative charges), and their propensity to aggregate in solution due to the relative large proportion of non-polar amino acid residues.

Peptide amphiphiles bearing the laminin-derived peptide sequence IKVAV (SEQ ID NO. 1) have been reported in the prior art to selectively differentiate neural stem cells into neurons, to promote neurite outgrowth, and to suppress differentiation into astrocytes in vitro. Furthermore, IKVAV-bearing peptide amphiphiles have been reported to promote axonal regeneration, improve motor function, reduce apoptosis and reduce astrogliosis in vivo in spinal cord lesions following spinal cord injury (SCI) in rodents. In addition, therapeutics incorporating the IKVAV (SEQ ID NO. 1) peptide may be used to treat other neurodegenerative conditions such as Parkinson's and Alzheimer's disease, by promoting regeneration of neurons from endogenous or exogenous neural stem cells. These compounds may also be used to minimize tissue damage or promote repair or regenerate of brain tissue following cerebral trauma or stroke.

The IKVAV (SEQ ID NO. 1) epitope has been shown to bind to at least two receptors, a 110 kDa laminin binding protein (LBP110/APP) and nucleolin, although the exact molecular arrangement of this binding and the signal transduction pathways are not known from the prior art. The IKVAV (SEQ ID NO. 1) peptide contains four hydrophobic amino acids with a strong propensity to form beta-sheet secondary and tertiary structures.

Peptides containing this epitope are reported to form amyloid-like fibrils. If the IKVAV (SEQ ID NO. 1) peptide epitope is hydrogen bonded in a rigid beta-sheet conformation with neighboring epitopes, this will likely reduce its ability to bind to target cellular receptors. While the IKVAV (SEQ ID NO. 1) peptide itself is known to promote neurite sprouting, in previous studies on IKVAV-bearing polymer scaffolds, enhanced neurite outgrowth and neuronal differentiation were not observed, possibly due to reduced epitope presentation resulting from unfavorable aggregation.

Thus, there exists a technological need, unfulfilled by the prior art, for an effective supramolecular strategy to control epitope presentation of hydrophobic bioactive peptides such as IKVAV (SEQ ID NO. 1) to enhance signal transduction.

Biologically active IKVAV-bearing PA molecules that may be purified using standard high performance liquid chromatography (HPLC) techniques are also needed. There is furthermore a need to develop IKVAV-bearing PAs that are soluble in salt solutions similar to extracellular fluid, in order to facilitate injection of PA solutions into living tissue.

SUMMARY OF THE INVENTION

Accordingly, it is an objective of the present invention to provide improved IKVAV-bearing peptide amphiphile (PA) molecules and self-assembled nanostructures having superior solubility and biological activity. In certain embodiments, PA nanofibers of the present invention are designed to not only incorporate molecular signals, such as the hydrophobic peptide epitope IKVAV (SEQ ID NO. 1), but also to effectively enhance their display on the surface of nanoscale aggregates, such as cylindrical micelles, nanofibers, trimer ribbons and bundles. In context of the present invention, nanostructure bundling, which unfavorably reduces bioactivity of the peptide epitope, is suppressed by electrostatic forces through the incorporation of appropriately placed ionizable side-chain residues.

It will be understood by those skilled in the art that one or more aspects of this invention can meet certain objectives, while one or more other aspects can meet certain other objectives. Each objective may not apply equally, in all its respects, to every aspect of this invention. As such, the following objects can be viewed in the alternative with respect to any one aspect of this invention.

It is an object of the present invention to provide PA molecules that utilize electrostatics to control the self-assembly behavior of PA molecules containing the hydrophobic IKVAV (SEQ ID NO. 1) epitope. In a preferred embodiment, PAs of the present invention contain an acyl group derived from palmitic acid, a beta-sheet forming peptide segment comprising the amino acid sequence Valine-Valine-Alanine-Alanine (VVAA) (SEQ ID NO. 2), a charged peptide sequence comprising two or more, and preferably three or more, and more preferably four or more glutamic acid (E) residues and one or more glycine (G) residues, and the peptide epitope IKVAV (SEQ ID NO. 1). It is furthermore an object of the present invention to formulate compositions of IKVAV-bearing PAs mixed with similar beta-sheet forming PAs that do not contain the IKVAV (SEQ ID NO. 1) epitope. These formulations enable the density of IKVAV (SEQ ID NO. 1) epitopes within the self-assembled nanostructures to be modulated.

A schematic illustrating preferred embodiments of the present invention is shown in FIG. 1. These peptide amphiphiles include:

While not wishing to be bound by theory, a key element of the design of PAs of the present invention is the increased number of charged amino acid residues (such as Glu), disposed near to the IKVAV (SEQ ID NO. 1) segment, which increases electrostatic repulsion and thereby reduces the propensity for unfavorable beta-sheet aggregation of the IKVAV (SEQ ID NO. 1) epitope. The number of glutamic acids (E) between the beta-sheet region and the IKVAV (SEQ ID NO. 1) sequence was increased in comparison to previously disclosed compounds to improve solubility and to enhance electrostatic repulsion between molecules, as well as to reduce inter-fiber aggregation (aggregation between different fibers). While not wishing to be bound by theory, inter-fiber aggregation is believed to play a role in the poor solubility and limited bioactivity of some previously disclosed IKVAV-bearing Pas containing only one or two acidic amino acid residues.

Another key element of the design of PAs of the present invention is the interposition of one or more Gly residue between the charged amino acid residues and the IKVAV (SEQ ID NO. 1) epitope. While not wishing to be bound by theory, it is anticipated that the inclusion of one or more Gly (G) residues prevents salt-bridge formation between the Glu and the Lys amino acid side-chains by altering side-chain orientation of these residues relative to each other, improving solubility of the peptide in salt solutions of similar composition to extracellular fluid. In one embodiment, the PAs of the present invention have one Gly residue between the charged amino acid residues (such as Glu) and the IKVAV epitope. In peptides of the present invention, Glu and Lys side-chains extend in opposite directions from the hydrogen bonded peptide backbone within a beta-sheet configuration, because of the interposed Gly-Ile residues.

In a certain embodiments, compounds of the present invention comprise the peptide sequences VVAAEEEGIKVAV (SEQ ID NO. 5) or VVAAEEEEGIKVAV (SEQ ID NO. 7). Peptide amphiphiles comprising these sequences are shown to be soluble in a physiologically relevant, monovalent salt solution composed of 150 mM NaCl and 3 mM KCl, and to promote neurite outgrowth in vitro. One of these compounds, with four Glu (E) residues, undergoes a transition from spherical micelles in a monovalent salt solution to isolated cylindrical micelles when calcium chloride is added to the solution, which is favorable for biological activity of the compounds in the CNS, where calcium ions are naturally abundant.

It is a further object of the present invention to provide biocompatible, biodegradable surface coatings or gels composed of peptide amphiphiles and/or peptide-amphiphile compositions, such surface coatings or gels being useful in $CH_3(CH_2)_{14}C(O)$-VVAAEE-$NH_2$ (SEQ ID NO. 3, termed herein PA 1)

$CH_3(CH_2)_{14}C(O)$-VVAAEEGIKVAV-OH (SEQ ID NO. 4, termed herein PA 2)

$CH_3(CH_2)_{14}C(O)$-VVAAEEEGIKVAV-OH (SEQ ID NO. 5, termed herein PA 3)

$CH_3(CH_2)_{14}C(O)$-VVAAEEEGGIKVAV-OH (SEQ ID NO. 6, termed herein PA 4)

$CH_3(CH_2)_{14}C(O)$-VVAAEEEEGIKVAV-OH (SEQ ID NO. 7, termed herein PA 5)

The VVAA (SEQ ID NO. 2) beta-sheet forming region is particularly preferred over previously disclosed peptides, in that it promotes desirable mechanical properties of PA gels by promoting beta sheet formation while limiting the total number of hydrophobic amino acids in the compound.

the creation of scaffolds or templates, which may or may not include isolated cells, and to introduce such scaffolds into a human patient to create or induce the body to create an organ or tissue equivalent. Such gels could promote cell engraftment and provide three-dimensional templates for new tissue growth. The resulting tissue is expected to be generally similar in composition and histology to naturally occurring tissue, in contrast to scar tissue that would generally result absent intervention during the body's natural healing process.

To that end, the present invention provides in one embodiment a self-assembling peptide-amphiphile solution than can be directly injected into a target site within a human patient, wherein the self-assembled peptide-amphiphile gel organizes into a nanofiber scaffold or matrix, the bundling and interdigitation of said nanofibers influenced by the peptide sequence selected. In another embodiment, cells may be suspended in a self-assembled peptide-amphiphile gel that is pre-formed into a matrix outside the body, which then can be implanted into a human patient. Ultimately, the self-assembled peptide-amphiphile gel degrades, leaving only the resulting tissue. In yet another embodiment of the present invention, the peptide-amphiphiles of the present invention are used in conjunction with other tissue engineering materials, either as a gel, solid, or liquid and are used to template tissue growth in a pre-determined area on a patient.

In certain embodiments, the present invention provides peptide amphiphile compounds comprising four segments: (1) a hydrophobic segment comprising an acyl group of six or more carbons, (2) a β-sheet-forming peptide segment; (3) a charged peptide segment, and (4) a signaling epitope. In some embodiments, the beta-sheet peptide segment comprises VVAA (SEQ ID NO. 2). In further embodiments, the charged peptide segment comprises $(E)_x(G)_y$, wherein x is 2 to 6 and y is 1. In further embodiments, the charged peptide segment comprises $(E)_x(G)_y$, wherein x is 2 to 4 and y is 1. In other embodiments, the signaling epitope comprises the peptide IKVAV (SEQ ID NO. 1). In additional embodiments, the signaling epitope comprises a peptide selected from among IKVAV (SEQ ID NO. 1), VAVKI (SEQ ID NO. 8), d(VAVKI) (SEQ ID NO. 9), VVIAK (SEQ ID NO. 10), and CRKQAASIKVAVSADR (SEQ ID NO. 11). In further embodiments, the signaling epitope consists of the peptide IKVAV (SEQ ID NO. 1). In other embodiments, the beta-sheet peptide sequence is selected from: VVAAEEGIKVAV (SEQ ID NO. 4), VVAAEEEGIKVAV (SEQ ID NO. 5), VVAAEEEEGIKVAV (SEQ ID NO. 6), or VVAAEEEE-GIKVAV (SEQ ID NO. 7). In particular embodiments, the hydrophobic segment is an acyl group derived from palmitic acid.

In some embodiments, the present invention provides compositions comprising: a) a first peptide amphiphile compound comprising four segments: (1) a hydrophobic segment comprising an acyl group of six or more carbons, (2) a β-sheet-forming peptide segment; (3) a charged peptide segment, and (4) a signaling epitope; and b) a second peptide amphiphile comprising the peptide sequence $(V)_x(A)_y(E)_z$-NH$_2$, wherein x=y=z=2.

In particular embodiments, the first and/or second peptide amphiphiles are self-assembled into one or more nanostructures, including cylindrical micelles, nanofibers, trimer ribbons, helical bundles or interdigitated nanofibers.

In further embodiments, the present invention provides methods of treating a subject comprising administering a pharmaceutical formulation to the subject, wherein the pharmaceutical formulation comprises a first peptide amphiphile compound comprising four segments: (1) a hydrophobic segment comprising an acyl group of six or more carbons, (2) a β-sheet-forming peptide segment; (3) a charged peptide segment, and (4) a signaling epitope.

In certain embodiments, the vehicle comprises a salt solution of composition similar to physiological extracellular fluid. In other embodiments, the physiological fluid is supplemented with multivalent ions, such as calcium ions, in order to electrostatically screen the charged peptide segment and promote beta-sheet self-assembly. In some embodiments, the pharmaceutical formulation further comprises a second peptide amphiphile comprising the peptide sequence $(V)_x(A)_y(E)_z$-NH$_2$, wherein x=y=z=2.

These and other objects and features of the invention will become more fully apparent when the following detailed description is read in conjunction with the accompanying figures and examples. However, it is to be understood that both the foregoing summary of the invention and the following detailed description are of a preferred embodiment, and not restrictive of the invention or other alternate embodiments of the invention. In particular, while the invention is described herein with reference to a number of specific embodiments, it will be appreciated that the description is illustrative of the invention and is not constructed as limiting of the invention.

Various modifications and applications may occur to those who are skilled in the art, without departing from the spirit and the scope of the invention, as described by the appended claims. Likewise, other objects, features, benefits and advantages of the present invention will be apparent from this summary and certain embodiments described below, and will be readily apparent to those skilled in the art having knowledge of various amphiphilic compounds, self-assembly techniques and peptide synthesis. Such objects, features, benefits and advantages will be apparent from the above as taken into conjunction with the accompanying examples, data, figures and all reasonable inferences to be drawn therefrom, alone or with consideration of the references incorporated herein.

BRIEF DESCRIPTION OF THE DRAWINGS

Various aspects and applications of the present invention will become apparent to the skilled artisan upon consideration of the brief description of the figures and the detailed description of the present invention and its preferred embodiments that follows:

FIG. 15 shows the average neurite lengths of neurons cultured in peptide amphiphile gels. The Y-axis indicates the neurite length relative to that of PA 1. n>59 for each bar. * indicates p-value <0.01 for the comparison with PA 1 (which does not contain the IKVAV epitope), ^ indicated a p-value <0.05 for the comparison with PA 3 (which contains the IKVAV epitope and forms interdigitaded trimer bundles).

DETAILED DESCRIPTION OF THE PREFERRED EMBODIMENTS

Figure 1:
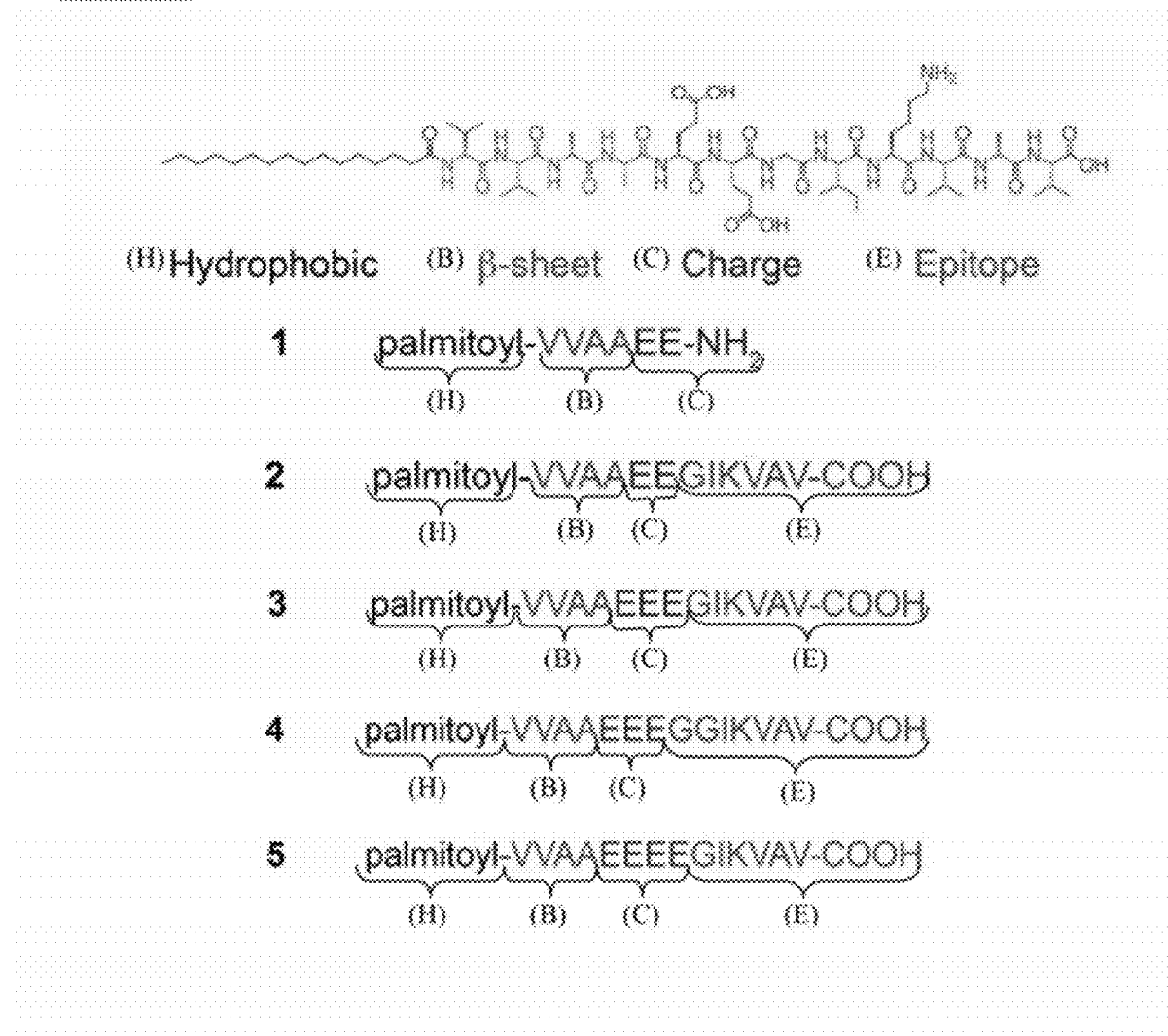
FIG. 1 depicts the chemical structures of peptide amphiphiles referred to herein as compounds 1-5 (SEQ ID NOs. 3-7). Peptide amphiphile design is illustrated, including the hydrophobic group, β-sheet forming peptide segment, charged peptide segment, and a bioactive IKVAV epitope.

Although any methods and materials similar or equivalent to those described herein can be used in the practice or testing of embodiments of the present invention, the preferred methods, devices, and materials are now described. However, before the present materials and methods are described, it is to be understood that this invention is not limited to the particular molecules, compositions, methodologies or protocols herein described, as these may vary in accordance with routine experimentation and optimization. It is also to be understood that the terminology used in the description is for the purpose of describing the particular versions or embodiments only, and is not intended to limit the scope of the present invention.

Unless otherwise defined, all technical and scientific terms used herein have the same meaning as commonly understood by one of ordinary skill in the art to which this invention belongs. However, in case of conflict, the present specification, including definitions, will control. Accordingly, in the context of the present invention, the following definitions apply:

As used herein and in the appended claims, the singular forms "a", "an" and "the" include plural reference unless the context clearly dictates otherwise. Thus, for example, reference to a "cell" is a reference to one or more cells and equivalents thereof known to those skilled in the art, and so forth.

As used herein, the term "nanofiber" refers to an elongated or threadlike filament having a diameter of less than 100 nanometers.

As used herein, the term "cylindrical micelle" refers to a colloidal aggregate with a non-spherical, high-aspect-ratio shape (length/diameter>10), composed of amphiphilic molecules in which the hydrophobic (or lipophilic) part of the amphiphiles forming the micelle tends to locate away from the polar phase (e.g. water) while the polar parts of the molecule (head groups) tend to locate at the micelle-solvent interface.

As used herein, the term "physiological conditions" refers to the range of conditions of temperature, pH and tonicity (or osmolality) normally encountered within tissues in the body of a living human.

As used herein, the terms "self-assemble" and "self-assembly" refer to formation of a discrete, non-random, aggregate structure from component parts; said assembly occurring spontaneously through random movements of the components (e.g. molecules) due only to the inherent chemical or structural properties of those components.

As used herein, the terms "scaffold" and "matrix" refer interchangeably to a natural or synthetic structure or meshwork of structures with open porosity that is extended in space and provides mechanical or other support for the growth of living tissue, either in the body or in vitro.

As used herein, the term "gel" refers to a semi-solid, viscoelastic material (capable of resisting some mechanical stress without deformation), which is formed by the coagulation of a colloidal liquid, consisting of a fibrous matrix and fluid-filled interstices.

As used herein, the term "peptide amphiphile" refers to a molecule that, at a minimum, includes a non-peptide lipophilic segment, a structural peptide segment and a functional peptide segment. The peptide amphiphile may express a net charge at physiological pH, either a net positive or negative net charge, or may be zwitterionic (i.e., carrying both positive and negative charges). Certain peptide amphiphiles consist or comprise four segments: (1) a hydrophobic, non-peptidic segment comprising an acyl group of six or more carbons, (2) a β-sheet-forming peptide segment; (3) a charged peptide segment, and (4) a signaling epitope.

As used herein and in the appended claims, the term "hydrophobic component" refers to the acyl moiety disposed on the N-terminus of the peptide amphiphile. This lipophilic segment may be herein and elsewhere referred to as the lipophilic component or hydrophobic segment. The hydrophobic component should be of a sufficient length to provide amphiphilic behavior and micelle formation in water or another polar solvent system.

Accordingly, in the context of the present invention, the hydrophobic component preferably comprises a single, linear acyl chain of the formula: $C_{n-1}H_{2n-1}C(O)$— where n=6-22. A particularly preferred single, linear acyl chain is the lipophilic group, palmitic acid $(C_{15}H_{31}C(O)$—). However, other small lipophilic groups may be used in place of the acyl chain.

As used herein, the term "structural peptide" or "beta-sheet forming peptide" refers to the intermediate amino acid sequence of the peptide amphiphile molecule between the hydrophobic segment and the charged peptide segment of the peptide amphiphile. This "structural peptide" or "beta-sheet forming peptide" is generally composed of three to ten amino acid residues with non-polar, uncharged side chains, selected for their propensity to form a beta-sheet secondary structure. Examples of suitable amino acid residues selected from the twenty naturally occurring amino acids include Met (M), Val (V), Ile (I), Cys (C), Tyr (Y), Phe (F), Gln (Q), Leu (L), Thr (T), Ala (A), Gly (G), (listed in order of their propensity to form beta sheets). However, non-naturally occurring amino acids of similar beta-sheet forming propensity may also be used. In a preferred embodiment, the N-terminus of the structural peptide segment is covalently attached to the oxygen of the lipophilic segment and the C-terminus of the structural peptide segment is covalently attached to the N-terminus of the charged peptide segment. In the context of the present invention, one particularly preferred structural peptide segment has the amino acid sequence VVAA (SEQ ID NO. 2). This structural segment is utilized in the exemplary peptide amphiphiles of the present invention.

As used herein, the term "charged peptide segment" refers to the intermediately disposed peptide sequence between the structural peptide segment or beta-sheet forming segment and the epitope. The charged peptide segment contains two or more amino acid residues that have side chains that are ionized under physiological conditions, examples of which selected from the 20 naturally occurring amino acids include Lys (K), Arg (R), Glu (E) and/or Asp (D), along with other uncharged amino acid residues. Non-natural amino acid residues with ionizable side chains could be used, as will be evident to one ordinarily skilled in the art. In one embodiment, the charged peptide segment contains two Glu (E) residues. In another embodiment, the charged peptide segment contains three Glu (E) residues.

One or more Gly (G) residues may be added to the "charged peptide segment," intermediately disposed between the charged residues and the "signaling epitope" discussed in greater detail below. While not wishing to be bound by theory, the inclusion of one or more Gly (G) residues appears to prevent salt-bridge formation between the Glu and the Lys amino acid side-chains by altering side-chain orientation of these residues relative to each other, improving solubility of the peptide in salt solutions of similar composition to extracellular fluid. In one embodiment, the charged peptide segments have the formula $(E)_x(G)_y$, wherein x is 2 to 6 and y is 1 to 6. In another embodiment, the charged peptide segment has 2 to 4 Glu (E) residues and 1 to 2 Gly (G) residues. In another aspect, the charged peptide segment has 2 Glu (E) residues and 1 Gly (G) residue. In yet another aspect of the invention, the charged peptide segment has 3 Glu (E) residues and 1 Gly (G) residue. In another embodiment, the charged peptide segment has 4 Glu (E) residues and 1 Gly (G) residue.

As used herein, the term "signaling epitope" is preferably a peptide sequence capable of selectively differentiating neural stem cells into neurons, promoting neurite outgrowth, and suppressing differentiation into astrocytes in vitro. Peptide amphiphiles bearing a laminin-derived signaling epitope such as IKVAV (SEQ ID NO. 1) have been reported to promote axonal regeneration, improve motor function, reduce apoptosis and reduce astrogliosis in vivo in spinal cord lesions following spinal cord injury (SCI) in rodents. In addition, therapeutics incorporating the IKVAV (SEQ ID NO. 1) peptide may be used to treat other neurodegenerative conditions such as Parkinson's and Alzheimer's disease, by promoting regeneration of neurons from endogenous or exogenous neural stem cells. These compounds may also be used to minimize tissue damage or promote repair or regenerate of brain tissue following cerebral trauma or stroke.

Variations on the IKVAV peptide epitope are possible by substituting one or more of the non-polar amino acid residues (V, A, or I), with another, similarly non-polar residue, including but not limited to I, A, G, V, or L. As will be understood by one skilled in the art, these and similar modifications may potentially retain the biological function of the original IKVAV (SEQ ID NO: 1) peptide sequence. Furthermore, some aspects of the present invention may utilize reverse (VAVKI) (SEQ ID NO. 8) or retro-inverse $_D$(VAVKI) (SEQ ID NO. 9) epitopes or scrambled epitopes such as VVIAK (SEQ ID NO. 10). Such changes may alter the epitope's ability to specifically bind its corresponding receptor, growth factor, etc. and thus may change (i.e., increase or decrease) the original biological function of the peptide, depending on the particular arrangement employed. In some instances of the present invention, it may be advantageous to use a longer portion of the peptide sequence from the laminin 1α chain, such as CRKQAASIKVAVSADR (SEQ ID NO. 11) or a portion thereof. These functional peptide segments may further include other known segments, in their original, reversed or scrambled form, provided that it retains the amphiphilic peptide molecules' ability to bind the functional peptide segments' corresponding receptor, growth factor, or the like.

Amino acids useful in the peptide amphiphiles of the present invention include but are not limited to naturally occurring amino acids and artificial amino acids. Incorporation of artificial amino acids such as beta or gamma amino acids and those containing non-natural side chains, and/or other similar monomers such as hydroxyacids are also contemplated, with the effect that the corresponding component is peptide-like in this respect.

The peptide amphiphile molecules and compositions of the present invention can be synthesized using preparatory techniques well-known to those skilled in the art, preferably, by standard solid-phase peptide synthesis, with the addition of a fatty acid in place of a standard amino acid at the N-terminus of the peptide, in order to create the lipophilic segment. Synthesis typically starts from the C-terminus, to which amino acids are sequentially added using either a Rink amide resin (resulting in an —NH$_2$ group at the C-terminus of the peptide after cleavage from the resin), or a Wang resin (resulting in an —OH group at the C-terminus). Accordingly, the present invention encompasses peptide amphiphiles having a C-terminal moiety that may be selected from the group consisting of —H, —OH, —COOH, —CONH$_2$, and —NH$_2$.

The lipophilic segment is typically incorporated at the N-terminus of the peptide after the last amino acid coupling, and is composed of a fatty acid or other acid that is linked to the N-terminal amino acid through an acyl bond. In aqueous solutions, PA molecules self-assemble into cylindrical micelles that bury the lipophilic segment in their core and display the functional peptide on the surface. The structural peptide undergoes intermolecular hydrogen bonding to form beta sheets that orient parallel to the long axis of the micelle. The cylindrical micelles (also referred to as nanofibers) can form gels in water or various aqueous media at concentrations ranging typically from 0.5 to 4 wt %.

To induce self-assembly of an aqueous solution of peptide amphiphiles, the pH of the solution may be changed (raised or lowered) or multivalent ions, such as calcium, or charged polymers or other macromolecules may be added to the solution. Though not intending to be bound by theory, self-assembly is facilitated in the instant case by the neutralization or screening (reduction) of electrostatic repulsion between ionized side chains on the charged peptide segment.

In one embodiment of the invention, the hydrophobic segment is $C_{15}H_{31}C(O)$—, the beta-sheet forming peptide is VVAA, the charged peptide segment is selected from EEG (SEQ ID NO:12), EEEG (SEQ ID NO:13), EEEGG (SEQ ID NO:14), and EEEEG (SEQ ID NO:15), and the epitope is IKVAV.

An embodiment of the invention is a PA comprising the formula $(V)_x(A)_y(E)_z$-NH$_2$, wherein V is valine, A is alanine, and E is glutamic acid. In this aspect of the invention, x is 1 to 6, y is 1 to 6, and z is 1 to 6. In another aspect of the invention, x is 2, y is 2, and z is 2-4. In yet another aspect of the invention, x is 2, y is 2, and z is 2. According to this aspect, the PA is $CH_3(CH_2)_{14}C(O)$-VVAAEE-$NH_2$ (SEQ ID NO. 3, termed herein PA 1). This PA may be used in combination with other peptide amphiphiles including the IKVAV epitope. For example, the PA 1 peptide amphiphile may be used in combination with $(CH_2)_{14}C(O)$-VVAAEEGIKVAV-OH (SEQ ID NO. 4, termed herein PA 2), $CH_3(CH_2)_{14}C(O)$-VVAAEEE-GIKVAV-OH (SEQ ID NO. 5, termed herein PA 3), $CH_3(CH_2)_{14}C(O)$-VVAAEEEGGIKVAV-OH (SEQ ID NO. 6, termed herein PA 4), and/or $CH_3(CH_2)_{14}C(O)$-VVAAEEEE-GIKVAV-OH (SEQ ID NO. 7, termed herein PA 5). The PA 1 molecule may be administered in combination with one or more of the other peptide amphiphiles or administered just prior to or subsequent to administration of one or more of the other peptide amphiphiles.

Another aspect of the invention is directed to a method of inducing the formation of isolated cylindrical micelles from spherical micelles by the introduction of multivalent ions, such as calcium. In particular, it has been found that the peptide amphiphile, VVAAEEEEGIKVAV (SEQ ID NO. 7), self-assembles into spherical micelles. However, this peptide amphiphile (SEQ ID NO: 7) undergoes a transition from spherical micelles in a monovalent salt solution to isolated cylindrical micelles when calcium chloride is added to the solution, which is favorable for biological activity of the compounds in the CNS, where calcium ions are naturally abundant.

In another aspect of the invention is a method of electrostatically controlling the bioavailability of PAs. PAs have been synthesized, wherein the epitope tends to aggregate on the nanofiber or with epitopes or other segments of neighboring molecules. According to this method, the PAs are engineered to reduced its propensity for epitope aggregation when they self-assemble into nanofibers. This method acts by controlling the assembly behavior of the PAs by increasing the number of charged amino acid residues preceding the epitope.

Therefore, in some embodiments, the method involves forming a self-assembling PA having a hydrophobic segment, a beta-sheet forming segment, a charged peptide segment and an epitope, wherein the charged peptide segment has an interdigitation-disrupting ability (e.g., by reducing epitope aggregation) without disrupting beta-sheet formation or self-assembly of the PA. In this embodiment, the charged peptide segment has the formula $(E)_x(G)_y$, wherein x is 2 to 6 and y is 1 to 6. In another embodiment, the charged peptide segment has 2 to 4 Glu (E) residues and 1 to 2 Gly (G) residues. In another aspect, the charged peptide segment has 2 Glu (E) residues and 1 Gly (G) residue. In yet another aspect of the invention, the charged peptide segment has 3 Glu (E) residues and 1 Gly (G) residue. In another embodiment, the charged peptide segment has 4 Glu (E) residues and 1 Gly (G) residue. In yet another embodiment of the invention, the hydrophobic segment is $C_{15}H_{31}C(O)$—, the beta-sheet forming peptide is VVAA, the charged peptide segment is selected from EEEG (SEQ ID NO:13) and EEEGG (SEQ ID NO:14, and the epitope is IKVAV. The PAs formed according to this method are then allowed to self-assembly into beta-sheet nanostructures with increased epitope availability.

In another embodiment, the present invention provides a method of treating a patient with tissue engineered material that includes the step of administering a peptide amphiphile composition to a target site on the patient in need of a tissue engineered material. One particularly preferred utility for the peptide amphiphile molecules and the gels formed therefrom is in the field of nerve regeneration and spinal cord injury treatment. PA compositions are capable of stimulating neural progenitor cell differentiation and of inhibiting scar tissue formation by CNS cells. PAs of the present invention may also find application in regulation, inhibition or promotion of axon outgrowth in neurons as well as the regulation, inhibition or promotion of cell-substrate adhesion among nerve cells.

It is a further object of the present invention to provide methods and compositions for altering (e.g., augmenting or stimulating) differentiation and growth of cells (e.g., neural stem cells and neurons). In particular, the present invention relates to compositions comprising one or more self-assembling peptide amphiphiles (e.g., in solution) that generate (e.g., self-assemble into) networks of isolated, non-interdigitated nanofibers that are able to encapsulate cells and promote cellular differentiation (e.g., neurite development) and methods of using the same. Compositions and methods of the present invention find use in research, clinical (e.g., therapeutic) and diagnostic settings.

In some embodiments, the present invention provides a method of altering development of a neuron comprising contacting the neuron with a composition comprising a peptide amphiphile. In some embodiments, altering development of a neuron comprises axonal growth, which can comprise descending motor fiber growth and/or ascending sensory fiber growth. In some embodiments, altering development occurs through a lesion site. In some embodiments, altering development of a neuron is accompanied by reduced astrogliosis. In some embodiments, the peptide amphiphile includes an IKVAV sequence and/or other amino acid sequence selected from the amino acid sequence of a laminin protein. In some embodiments, the neuron is a neuron in a spinal cord that has been damaged by traumatic injury. In some embodiments, altering development of a neuron involves promoting neurite sprouting or neurite outgrowth. In some embodiments, it involves increasing the length of developing neurites.

In other embodiments, the neuron is a neuron within the cortex of the brain. In some embodiments, the neuron is damaged due to stroke. In some embodiments the neuron is a dopaminergic neuron within the substantia nigra in the brain. In some embodiments, the neuron is damaged due to degenerative disease processes, including those in Parkinson's and Alzheimer's diseases.

It is a further object of the present invention to provide a method for treating a subject comprising the steps of: administering a composition comprising a mixture of peptide amphiphiles to a subject with a damaged nerve or nerves, under conditions such that neuron or neurite growth occurs in the subject. In some embodiments, the neuron growth comprises axonal growth of descending motor fibers and/or ascending sensory fibers. In some embodiments, the neuron growth comprises axonal growth at the site of the damaged nerve. In some embodiments, neuron growth comprises regeneration of cortex neurons or dopaminergic neurons in the brain. In some embodiments, the neuron growth is accompanied by reduced astrogliosis and associated scar tissue formation in the subject. In preferred embodiments, the reduced astrogliosis and the reduced scar formation occur at the site of nerve damage. In some embodiments, the damaged nerve is a nerve in a spinal cord that has been damaged. In some embodiments, the damaged nerve has been damaged by traumatic spinal cord injury. In some embodiments, the damaged nerve is in the peripheral nervous system. In some embodiments, the nerve damage is a result of a neurodegerative disease. In some embodiments, the damaged nerve comprises a damaged sensory neuron. In some embodiments, the damaged nerve comprises a damaged motor neuron. In some embodiments, neuron growth comprises regenerating development of a damaged neuron. In some embodiments, administering comprises intrathecal injection of an aqueous solution of the peptide amphiphile. In some embodiments, the peptide amphiphile forms a nanofiber gel upon contact with the damaged tissue. In some embodiments, the composition comprising a peptide amphiphile is co-administered with one or more other agents.

It is a further object of the present invention to provide pharmaceutical compositions comprising one or more peptide amphiphiles, for example those comprising an IKVAV (SEQ ID NO. 1) sequence. See U.S. Patent Publication No. 2006-0247165 (Stupp et al.), the contents of which are incorporated by reference herein.

Hereinafter, the present invention is described in more detail by reference to the Examples. However, the following materials, methods and examples only illustrate aspects of the invention and in no way are intended to limit the scope of the present invention. As such, methods and materials similar or equivalent to those described herein can be used in the practice or testing of the present invention.

EXAMPLES

Example 1

Peptide Amphiphile Synthesis and Purification

The PA compounds are referred herein as compounds 1 through 5, as shown in FIG. 1. PAs were synthesized using resins and Fmoc-protected amino acids purchased from Novabiochem Corporation. All other solvents were ACS reagent grade and purchased from Mallinckrodt and reagents were purchased from Aldrich and used as received. Manual solid-phase peptide synthesis was performed on a 0.5 mmole scale using 50 mL peptide synthesis vessels (Chemglass) and a wrist-action shaker. For 1, a Rink Amide resin was used. For 2-5, the initial valine acid was purchased preloaded as a Fmoc-Val Wang resin. For each coupling the Fmoc protecting group was removed by shaking the resin in 30% piperidine in N,N-dimethylformamide (DMF) for ten minutes, rinsed and repeated a second time. The resin was washed with dichloromethane (DCM) and DMF, and allowed to swell in DCM for 15 minutes before coupling. Amino acids were activated by adding 4 molar equivalents of the Fmoc-protected amino acids to 4 molar equivalents of O-benzotriazole-N,N,N',N'-tetramethyluronium hexafluorophosphate (HBTU) and dissolving in 30 ml of DMF. Six molar equivalents of diisopropylethylamine (DIEA) were added to the amino acid solution, which was allowed to sit for a minute before being added to the resin. The coupling reaction was allowed to proceed for three hours, at the end of which the resin was washed in DCM and DMF and ninhydrin tests were done to check for the presence of free amines. If the ninhydrin test yielded a positive result the coupling was repeated. The palmitoyl tail was added using same molar ratio of palmitic acid/HBTU/DIEA of 4:4:6. Alternatively, some PAs were synthesized on a CS Bio Co. automatic peptide synthesizer using a similar methodology, however with 90 minute coupling times. PAs were cleaved by shaking the resin in a peptide cleavage solution of 95% trifluoroacetic acid (TFA), 2.5% triisopropyl silane (TIS) and 2.5% $H_2O$ for three hours. The cleavage solution was drained into a round bottom flask and the resin was rinsed several times with DCM. All liquid was removed using rotary evaporation, and the PA residue was washed with cold diethyl ether and poured into a fritted filter. After the diethyl ether passed through the filter, the PA flakes were rinsed again with diethyl ether, allowed to dry and then placed in a vacuum desiccator until HPLC purification.

The PAs were then dissolved in 90% DI water and 10% of either acetonitrile or methanol at a concentration of 10-20 mg/mL. Ammonium hydroxide was added to the solution until pH was raised to 8-9. To assist in solubilization, the solutions were ultrasonicated in an ice bath, using a Branson horn ultrasonicator operating at 15% power for five minutes. The solution was then passed through a 0.22 micrometer filter and injected into a prep scale reverse phase HPLC running a mobile phase gradient of 90% H2O and either 10% acetonitrile (HPLC grade, Mallinckrodt) or methanol (HPLC grade, Mallinckrodt) to 100% acetonitrile or methanol, respectively. 0.1% $NH_4OH$ was added to all mobile phases to aid PA solubility. The Phenomenex C18 Gemini NX column had a 5 micron pore size, a 110 angstrom particle size and was 150× 30 mm HPLC fractions were checked for the correct compound using electrospray ionization mass spectroscopy (ESI-MS), rotary evaporated to remove acetonitrile and methanol, and lyophilized (Labconco, FreezeZone6) at a pressure 0.015 torr.

Example 2

Chemical Analysis of Peptide Amphiphiles

Peptide content analysis was performed on lyophilized samples following hydrolysis in 6N HCl at 110 C, to verify the stoichiometry and determine the residual salt concentration for compounds 1-5. The relative residue stoichiometry was within +/−5% of the expected values for all amino acids. The mg of total peptide amphiphile per mg of solid was determined and used to normalize concentration of the compounds in subsequent analysis. Identity and purity of the compounds was confirmed by analytical HPLC and ESI-MS.

Example 3

Circular Dichroism (CD)

CD was done using a model J-715 Jasco Circular Dichroism Spectrometer. 1 wt % PA solutions were prepared in either a 150 mM NaCl, 3 mM KCl solution or a 150 mM NaCl, 3 mM KCl, and 5 mM $CaCl_2$ solution, both at a pH of 7.2-7.4, as determined via pH paper. The solutions were then heated to 80° C. in a water bath for 1 hr, and then slowly cooled to room temperature over the course of 8 hr. The samples were measured through 0.01 mm quartz plates. Each trace represents the average of three scans. The mean residue ellipticity was corrected for purity of the lyophilized powder from peptide content analysis.

Example 4

Transmission Electron Microscopy of PA Nanostructures

The nanostructure of each PA molecule under physiologically relevant conditions was investigated using electron microscopy. Samples for vitreous ice cryo-transmission electron microscopy (cryoTEM) were prepared from a 0.1-0.5 wt % PA solution dissolved in 150 mM NaCl, 3 mM KCl, or in a 150 mM NaCl, 3 mM KCl, and 5 mM $CaCl_2$ solution, both at a pH of 7.2-7.4. The solutions were then heated to 80° C. in a water bath for 1 hr, and then slowly cooled to room temperature over the course of 8 hr. 10 μL of each solution was pipetted onto a plasma cleaned holey carbon TEM grid (Electron Microscopy Sciences), blotted and plunged into liquid ethane using a FEI Vitrobot Mark IV. Samples were kept at −180° C. and imaged using a JEOL 1230 TEM operating at 100 kV.

Samples for conventional TEM microscopy were prepared from 0.1 wt % PA solution dissolved in ultrapure water and adjusted to a pH of 7.2-7.4 by adding NaOH. The solutions were then heated to 80° C. in a water bath for 1 hr, and then slowly cooled to room temperature over the course of 8 hr, unless noted otherwise. 2 μL of a 0.1 wt % PA solution was pipetted onto a Carbon Formvar grid (Electron Microscopy Sciences) and allowed to dry. The samples were then negatively stained by pipetting 2 uL of a 2 wt % Uranyl acetate solution and allowed to dry. Each sample was imaged using a JEOL 1230 TEM operating at 100 kV. The average diameter of nanofibers was obtained via measuring 40-100 different fibers from solutions and grids prepared throughout multiple days.

Example 5

X-Ray Scattering of PA Nanostructures

Small-angle X-ray scattering (SAXS) measurements were obtained using a Rigaku S-MAX 3000 High Brilliance SAXS System. Cu Kα radiation was generated by Osmic Micro-Maxs, an integrated microfocus sealed tube generator (powered at 45 kV and 0.9 mA) with Osmict Confocal Max-Fluxs optics, 3 pinholes collimation. A 20×20 cm$^2$ 2D position-sensitive wire detector (1024×1024 pixels) was positioned 150 cm behind the examined samples, resulting in a q-range of 0.07-2.8 nm$^{-1}$. The wave vector defined as, $q=(4\pi/\lambda)\sin(2\theta/2)$, where 2y is the scattering angle and λ is wavelength of Cu K$_\alpha$ radiation (1.542 Å). A total of $10^6$ or more counts were collected in order to obtain a high signal to noise ratio. Samples were measured for 3600 s, and then background subtracted from data collected using a capillary containing the isotonic salt solution. The 2D SAXS patterns were azimuthally averaged and the background subtracted using standard methods. Data analysis was based on fitting the scattering curve to an appropriate model by a least-squares method using software provided by NIST (NIST SANS analysis version 7.0 on IGOR)[21] The table below lists the models used to fit the SAXS curves. The Total SAXS cross-sectional dimensions correspond to length and width for molecule 2, and diameter for 3-5.

| PA molecule | SAXS model | Core Diameter (nm) | Shell Thickness (nm) | Total SAXS Cross-section dimensions (nm) |
|---|---|---|---|---|
| 2 (SEQ ID NO: 4) | Rectangular ribbon | | | 6.0 × 18.0 |
| 3 (SEQ ID NO: 5) | (Core) Shell Cylinder | 1.2 | 3.8 ± 0.6 | 7.6 ± 1.2 |
| 4 (SEQ ID NO: 6) | (Core) Shell Cylinder | .93 | 2.63 ± 1.1 | 7.1 ± 2.2 |
| 5 (SEQ ID NO: 7) | (Core) Shell Sphere | 1.46 | 1.4 ± 0.6 | 5.9 ± 1.2 |
| 5 (SEQ ID NO: 7) | (Core) Shell Cylinder | 1.2 | 2.0 ± 0.6 | 6.4 ± 1.8 |

Wide-angle X-ray scattering (WAXS) was performed at Argonne National Laboratory at the BioCARS 14-BM-C beamline with 0.9787 Å X-ray radiation. 1 wt % PA solutions dissolved in either a 150 mM NaCl and 3 mM KCl solution, or a 150 mM NaCl, 3 mM KCl, and 5 mM CaCl$_2$ solution, adjusted to a pH of 7.2-7.4 by adding NaOH. The solutions were then heated to 80° C. in a water bath for 1 hr, and then slowly cooled to room temperature over the course of 8 hr. Each solution was loaded into a 1.0 mm quartz capillary, and sealed with epoxy. Samples were measured for 90 s, with a 100 mm beam-stop to sample distance a 600 mm sample to detector distance, and then background subtracted from data collected using a capillary containing the isotonic salt solution.

Example 6

PA Molecular Simulations

The molecular length of each peptide amphiphile was estimated through models derived from the MM$^+$ geometry optimization as implemented using the Hyperchem Software Suite. The molecule length was derived from the energy-minimized geometry of the fully extended molecule. The value for molecular length was assumed to be the distance between the final C atom on the alkyl chain and the end amide C atom on the terminal glutamic acid (for 1), or the end carboxylate carbon on the terminal valine (for 2-5).

Figure 2:
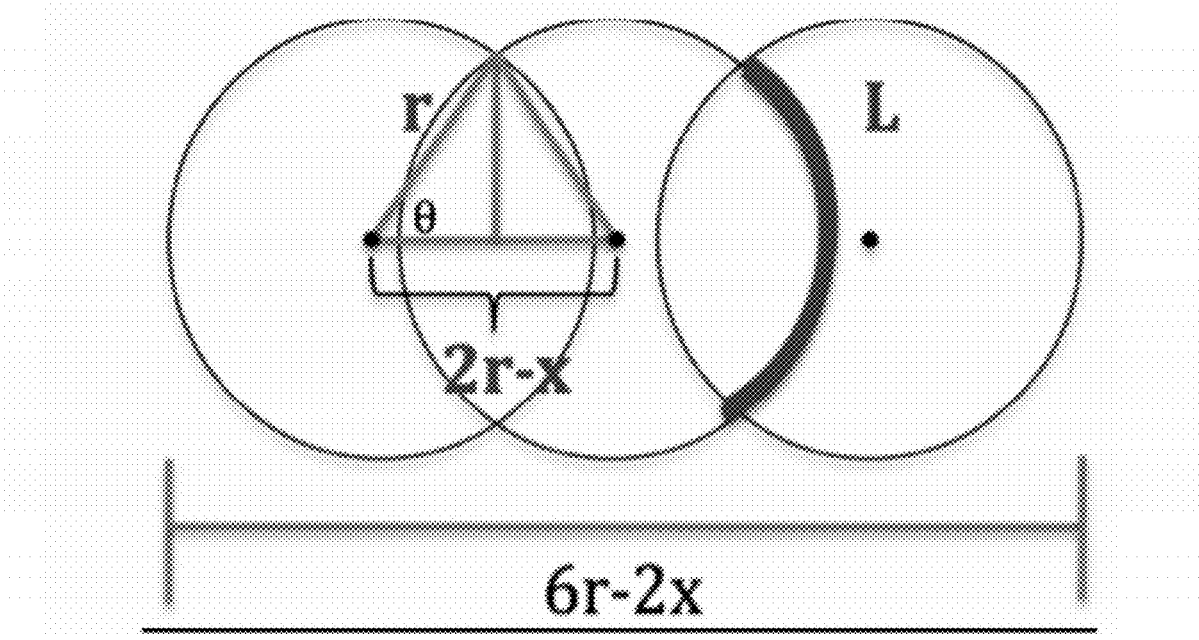
FIG. 2 depicts a schematic of the cross-section of a bundle of three nanofibers (termed a 'trimer') illustrating the geometric terms used to estimate the surface area of exposed and non-interdigitated IKVAV epitopes in this nanostructure configuration.

The percentage of nanofiber surface area that was not interdigitated in a bundled nanostructure was estimated from the observed TEM data and molecular simulations. The cross-section of a trimer bundled is shown in FIG. 2. In the Figure, r is the scaled simulated molecular length of the nanostructure (simulated molecular length*0.87, the scaling factor for TEM comparison) and x is the length of overlap between neighboring epitopes. To solve for x, the total width of the nanostructure (6r−2x) is equal to the observed trimer bundle width from TEM (18.0 nm). θ, or half the interdigitated arc angle, is equal to $\cos^{-1}((r-x/2)/r)$. The interdigitated arc length (L) is equal to 2θr, where θ is in units of radians. The percentage of non-interdigitated surface area is equal to $(3*2\pi r-4L)/(3*2\pi r)*100\%$. For dimer bundles, the total nanostructure width is given by (4r−x), and the percentage of non-interdigitated surface area is equal to $(2*2\pi r-2L)/(2*2\pi r)*100\%$. The table below lists the observed morphologies from TEM (Example 4), the simulated molecular length and scaled nanostructure diameter (described above) and the observed fiber diameter from TEM.

| PA | ASSEMBLED MORPHOLOGY | SIMULATED MOLECULAR LENGTH (Å) | SCALED, SIMULATED DIAMETER (Å) | OBSERVED FIBER DIAMETER (Å) |
|---|---|---|---|---|
| 1 | Cylindrical fiber | 38.0 | 66 | 66 ± 9 |
| 2 | Trimer ribbon | 55.5 | 97 | 60 ± 5 |
| 3 | Trimer ribbon | 59.6 | 104 | 71 ± 5 |
| 3 | Cylindrical assembly | 59.6 | 104 | 128 ± 14 |
| 4 | Dimer Bundle | 63.5 | 110 | 77 ± 9 |
| 4 | Triple helix | 63.5 | 110 | 81 ± 10 |
| 5 | Cylindrical fiber | 60.1 | 105 | 108 ± 15 |

Example 7

Figure 3:
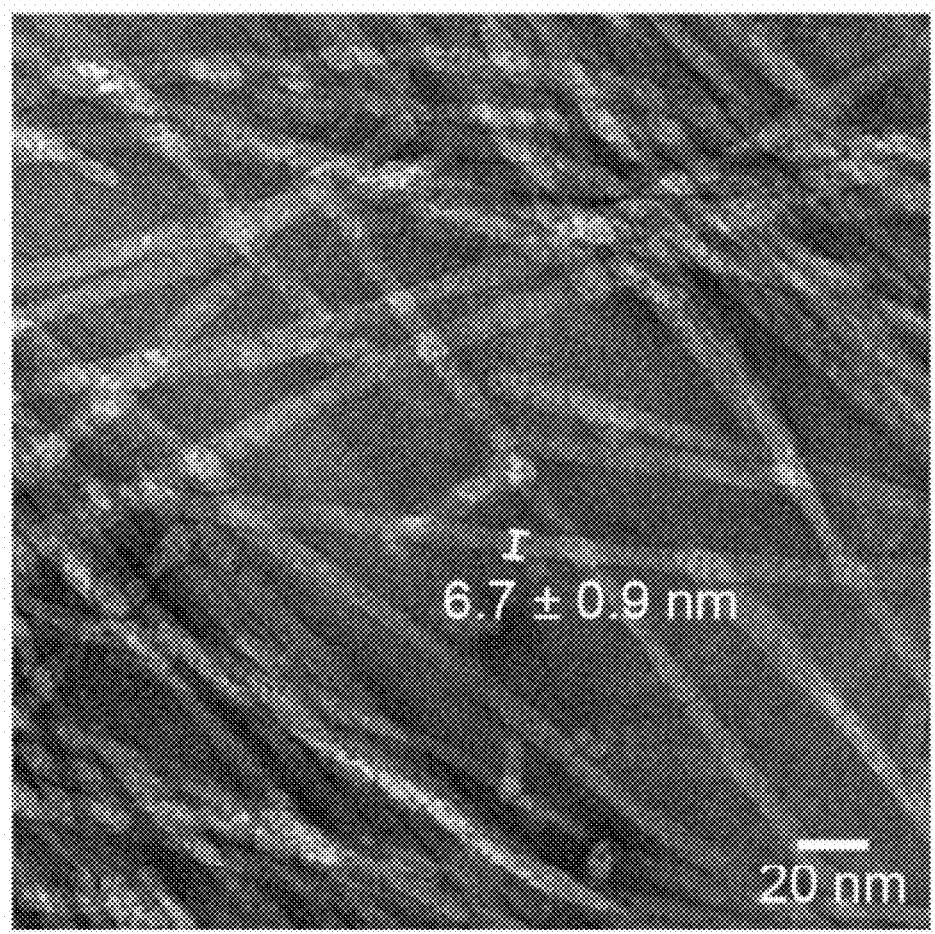
FIG. 3 depicts a schematic illustration of the peptide arrangement within the individual cylindrical nanofiber structure of PA compound 1, along with a TEM micrograph. The 6.7 nm nanofiber diameter indicated.

Hydrophobic IKVAV Epitope Promotes Interdigitated Beta-Sheet Aggregation in Solution The assembly of each PA molecule under physiologically relevant conditions was examined using cryogenic electron microscopy (cryoTEM), as described in Example 4. PAs were dissolved in isotonic salt solutions resembling extracellular fluid (150 mM NaCl, 3 mM KCl, pH 7.4). PA 1, which lacks the IKVAV epitope, assembles into typical cylindrical fibers that have an average diameter of 6.7±0.9 nm (see FIG. 3). This diameter is 87% of twice the length of 1, based on the MM+ molecular simulations described in Example 6, which corresponds approximately to the expected diameter of cylindrical fibers consisting of hydrophobically collapsed beta-sheets displaying the epitope on their surfaces. In order to compare molecular simulation diameters with those observed from TEM, molecular simulation values for the other four PA molecules were scaled by the same amount, 87%.

Figure 4:
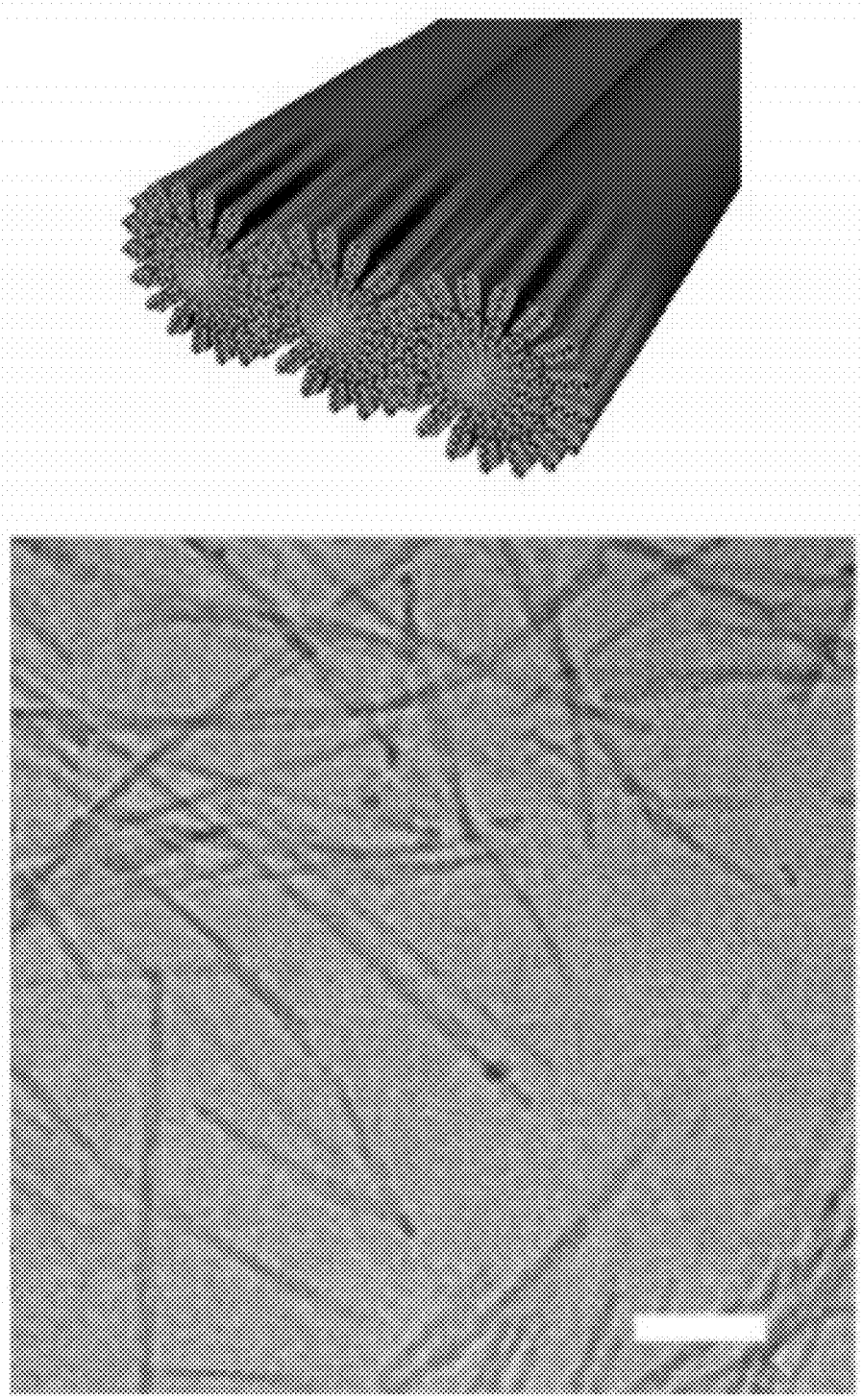
FIG. 4 is a cryoTEM image of PA 2 in aqueous salt solution, showing the ribbon-like morphology of the nanostructures observed. Scale bar is 100 nm.
Figure 5:
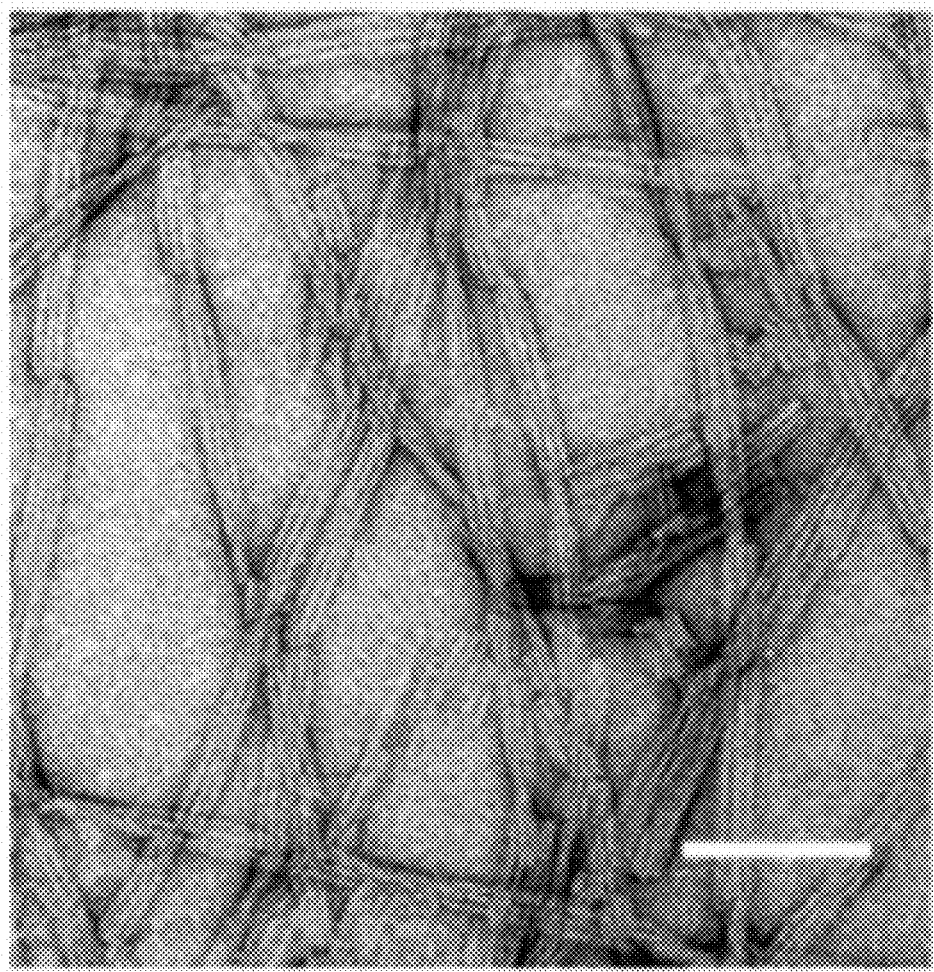
FIG. 5 depicts a schematic illustration of the peptide arrangement in an interdigitated, ribbon-like trimer bundle of three nanofibers, as observed for PA 2. Also shown is a TEM micrograph of the trimer bundles. Scale bar is 100 nm.
Figure 6:
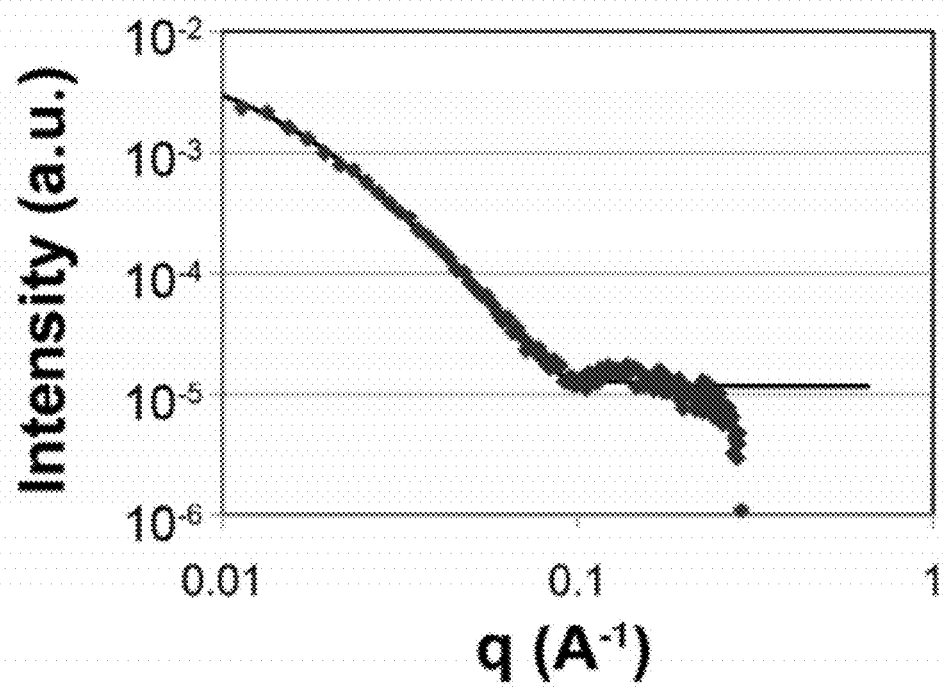
FIG. 6 depicts SAXS of PA 2 (dots) fit to a 6.0×18.0 nm nanoribbon cross-sectional model (line).

PA 2, which has the same sequence as PA 1 plus the addition of the IKVAV epitope, forms ribbon-like morphologies (see FIG. 4) in solution that are comprised of at least three cylindrical fibers, each 6.0±0.5 nm in diameter, aggregated side-by-side, as shown in FIG. 5. Modeling of the small angle x-ray scattering (SAXS) curve ($q<10^{-1}$ Å) obtained in Example 5 was experimentally fit to a ribbon morphology with 6.0×18.0 nm a rectangular cross-section (FIG. 6). This confirms that ribbons of three bundled cylindrical nanofibers are the dominant supramolecular architecture. The predicted diameter of fibers of 2 from simulations is 9.7 nm. Thus the fiber diameter reduction from 1 to 2 suggests that the hydrophobic IKVAV epitopes are interdigitated and form antiparallel beta-sheets with the VVAA core of neighboring fibers.

Example 8

Figure 7:
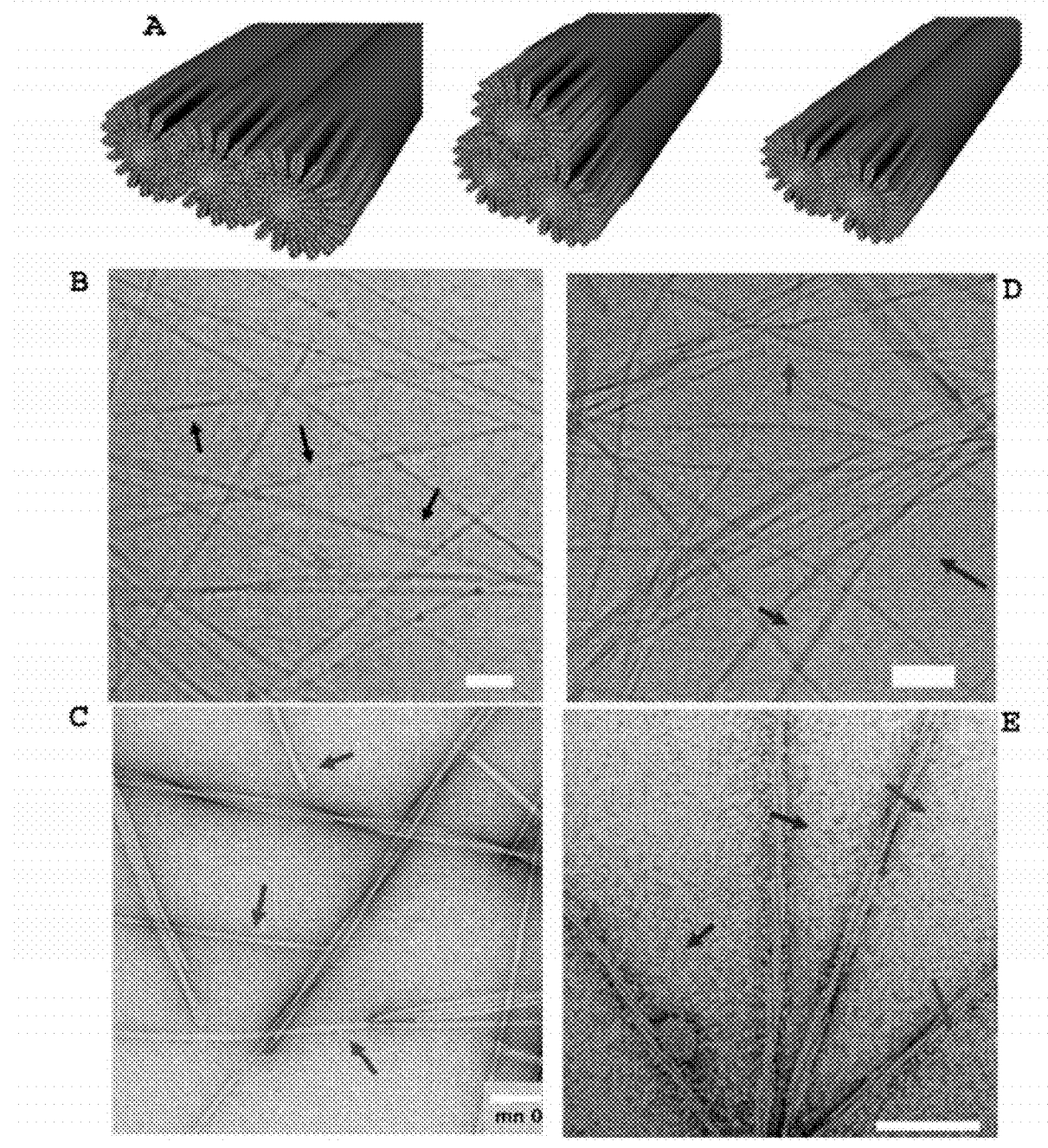
FIGS. 7A-E depict schematic illustrations (7A) of various interdigitated nanofiber morphologies observed in cryoTEM (FIGS. 7B and 7D) and conventional TEM (FIGS. 7C and 7E) of PA 3 (left) and PA 4 (right). Arrows point to trimer bundle motifs (FIG. 7B), cylindrical assemblies (FIG. 7C), triple helices (two lower arrows shown in FIG. 7D and two arrows on the left in FIG. 7E), and dimer bundle motifs (two upper arrows shown in FIG. 7D and two arrows on the right in FIG. 7E), respectively. All scale bars correspond to 100 nm.

Disruption of Interdigitated Nanofiber Aggregation by Increasing Electrostatic Repulsion In contract to PA 2, in which two glutamic acid residues were included in the charged peptide segment, in PAs 3 and 4, three glutamic acids are incorporated, and a mixture of different types of interdigitated assemblies is observed. CryoTEM and conventional TEM showed that 3 (FIG. 7, left images) assembled into a mixture of trimeric ribbons with fiber diameters of 7.1±1 nm as well as cylindrical assemblies with a 12.8±1.3 nm diameter. For the trimer ribbon motif, this increase in radius of 0.5 nm from 2 to 3 corresponds closely to the simulated increase in molecular length upon addition of an amino acid (~0.4 nm). The structure that appears as a cylindrical assembly does not correspond to a conventional cylindrical aggregate; the diameter is larger than the length expected from molecular simulations (10.4 nm), and there is a helical twist 8-12° along the vertical axis of the fiber, supporting the notion that this supramolecular assembly is larger than two molecules. PA 4, containing an additional glycine residue between the charged EEE and the IKVAV segments, also forms a mixture of aggregated fibers, including bundled dimers (FIG. 7, right images) consisting of 8.1±1.0 nm fibers, triple helices comprised of 7.7±0.9 nm diameter fibers, and larger aggregates.

Figure 8:
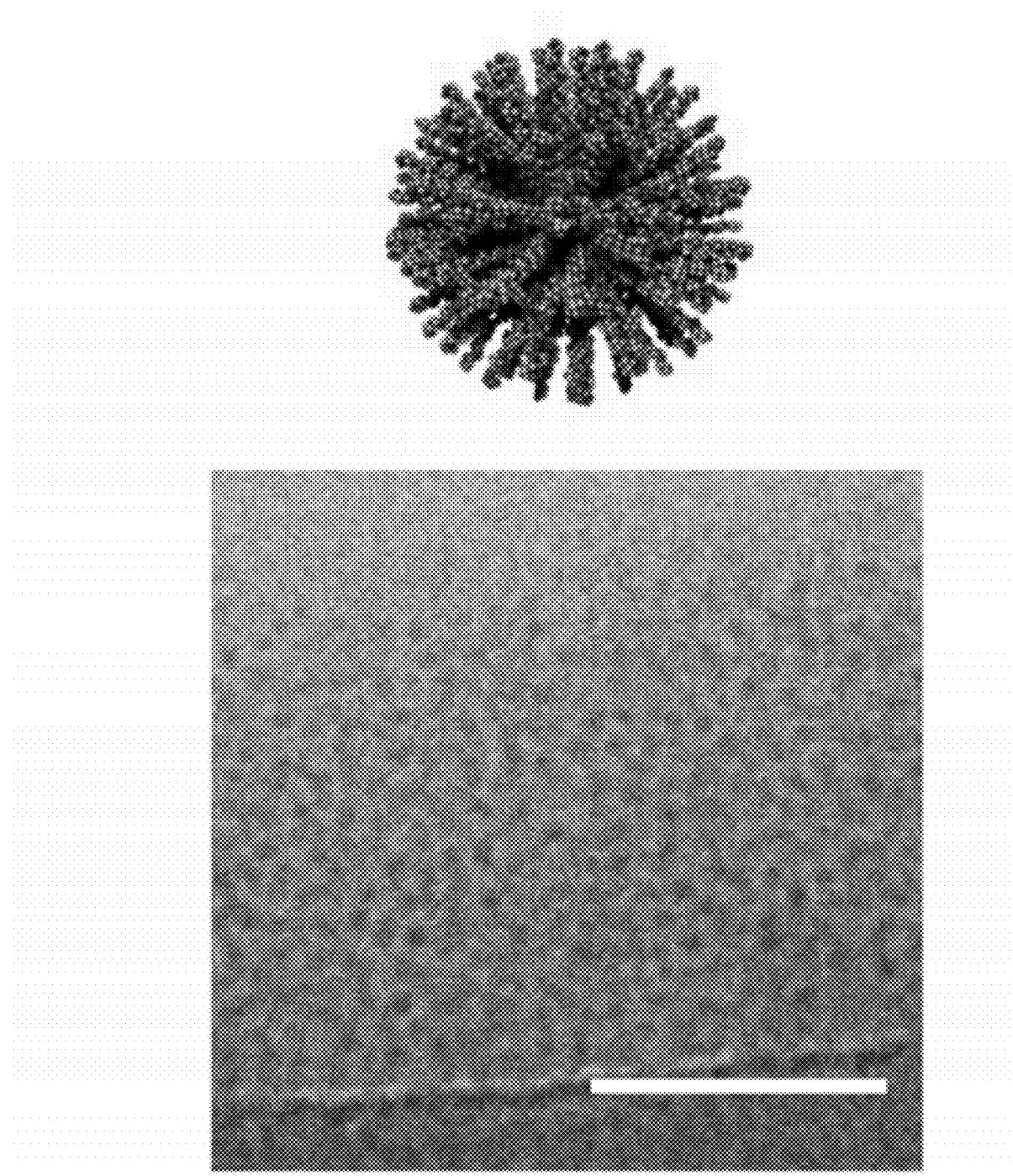
FIG. 8 depicts a schematic illustration of the peptide arrangement in a spherical micelle, as observed by TEM of PA compound 5 dissolved in water. Scale bar is 100 nm.
Figure 9:
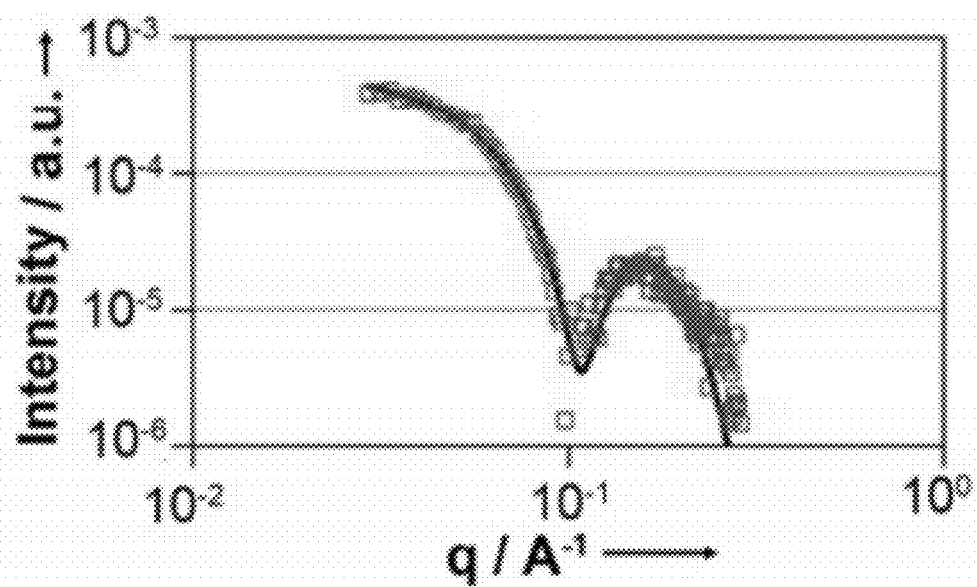
FIG. 9 depicts SAXS of PA 5 (squares) fit to a core-shell spherical micelle model (line) with a diameter of 5.9±1.2 nm.
Figure 10:
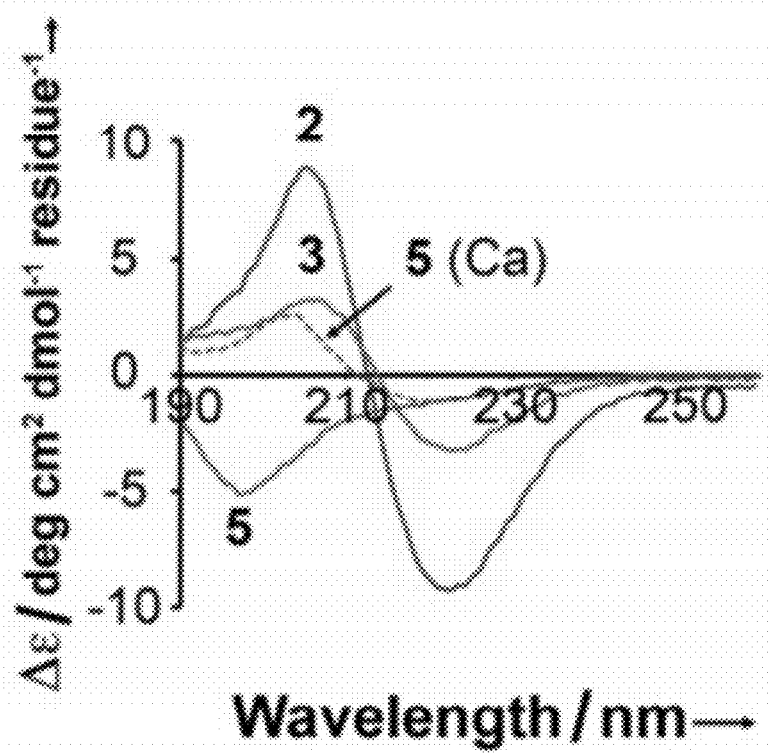
FIG. 10 depicts CD spectra of PA 2, 3 and 5 at 1 wt % dissolved in 150 mM NaCl, 3 mM KCl, and also PA 5 with the addition of 5 mM $CaCl_2$ denoted "5 (Ca)".
Figure 11A:
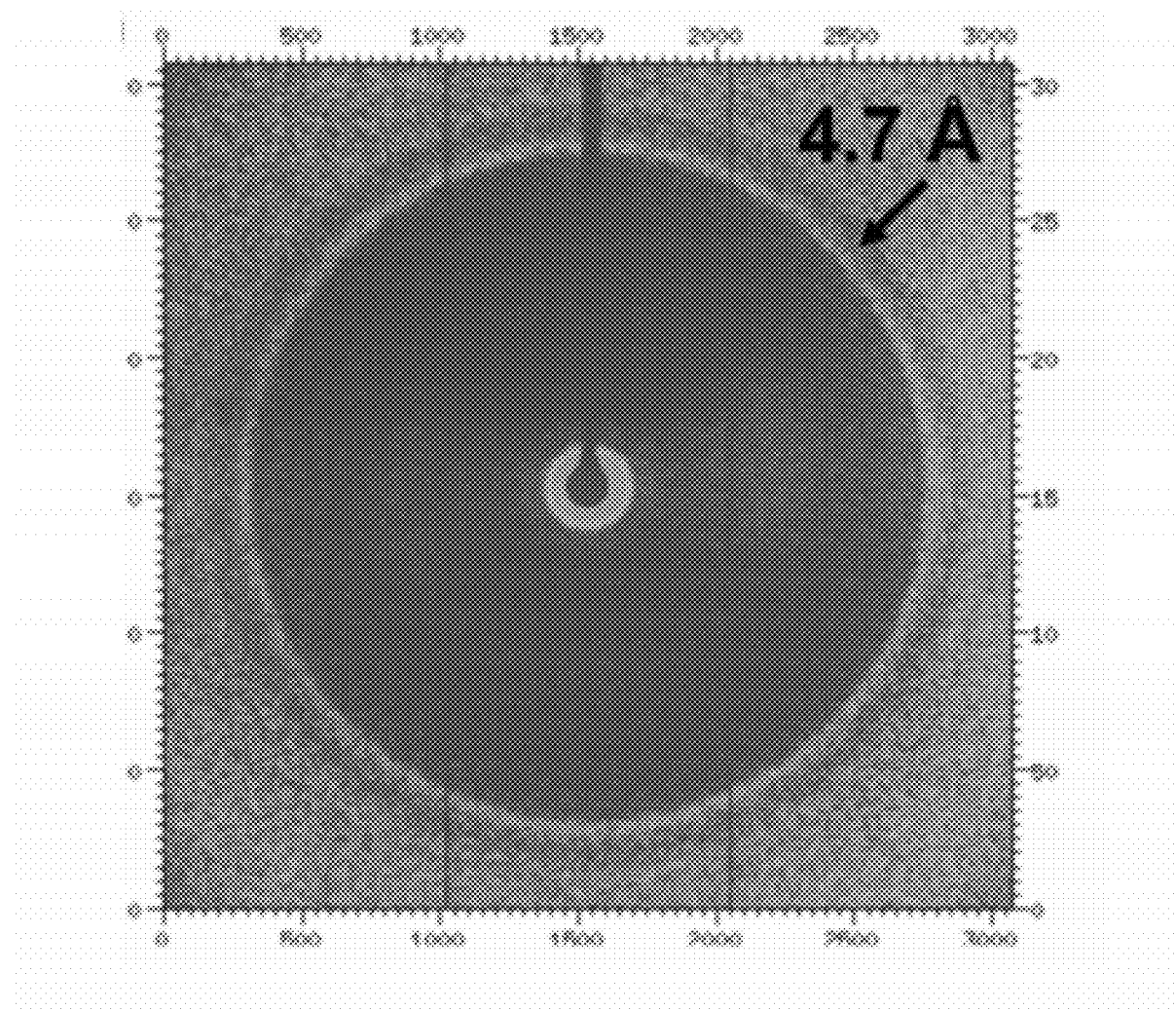
FIG. 11 depicts background-subtracted WAXS data obtained from 1 wt % solutions of a) PA 2 in 150 mM NaCl and 3 mM KCl, b) PA 5 in 150 mM NaCl and 3 mM KCl, and c) PA 5 in the same salt solution with added 5 mM $CaCl_2$. The 4.7 Å peak spacing observed is indicative of beta-sheet aggregation.
Figure 11B:
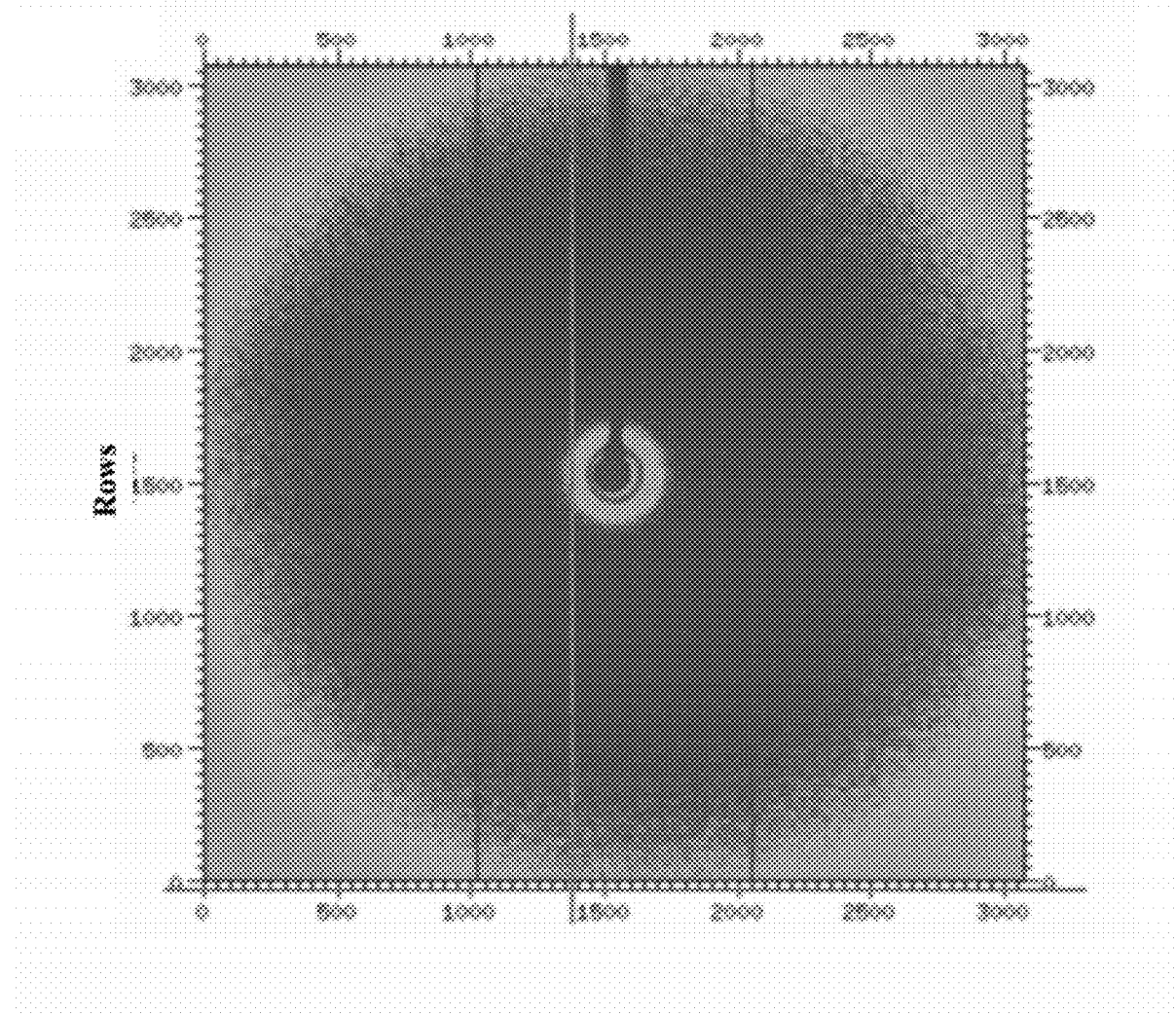

To fully disrupt interdigitation and increase presentation of the IKVAV epitope on the nanofiber surface, a fourth glutamic acid was added to the negatively charged peptide segment in PA 5. Surprisingly, this additional charged amino acid disrupted β-sheet formation and prevented self-assembly into nanofibers when the peptide was dissolved in water. Only spherical micelles having a diameter of 5.3±1.1 nm were observed in cryoTEM micrographs of 5 (see FIG. 8). Furthermore, the SAXS curve can be fit with a core-shell spherical micelle model with a diameter of 5.9±1.2 nm (FIG. 9). Dynamic light scattering data confirmed that solutions were comprised of spherical micelles with a hydrodynamic radius of 8.6 nm. The lack of positive ellipticity in the CD spectrum (Example 3) indicates that 5 has a random coil peptide structure in the supramolecular aggregates it forms, in contrast to PA 2 and 3, which show beta-sheet like CD signatures (FIG. 10). In addition, there is no β-sheet peak at 4.7 Å in the wide angle x-ray scattering (WAXS) curve (FIG. 11).

Figure 12:
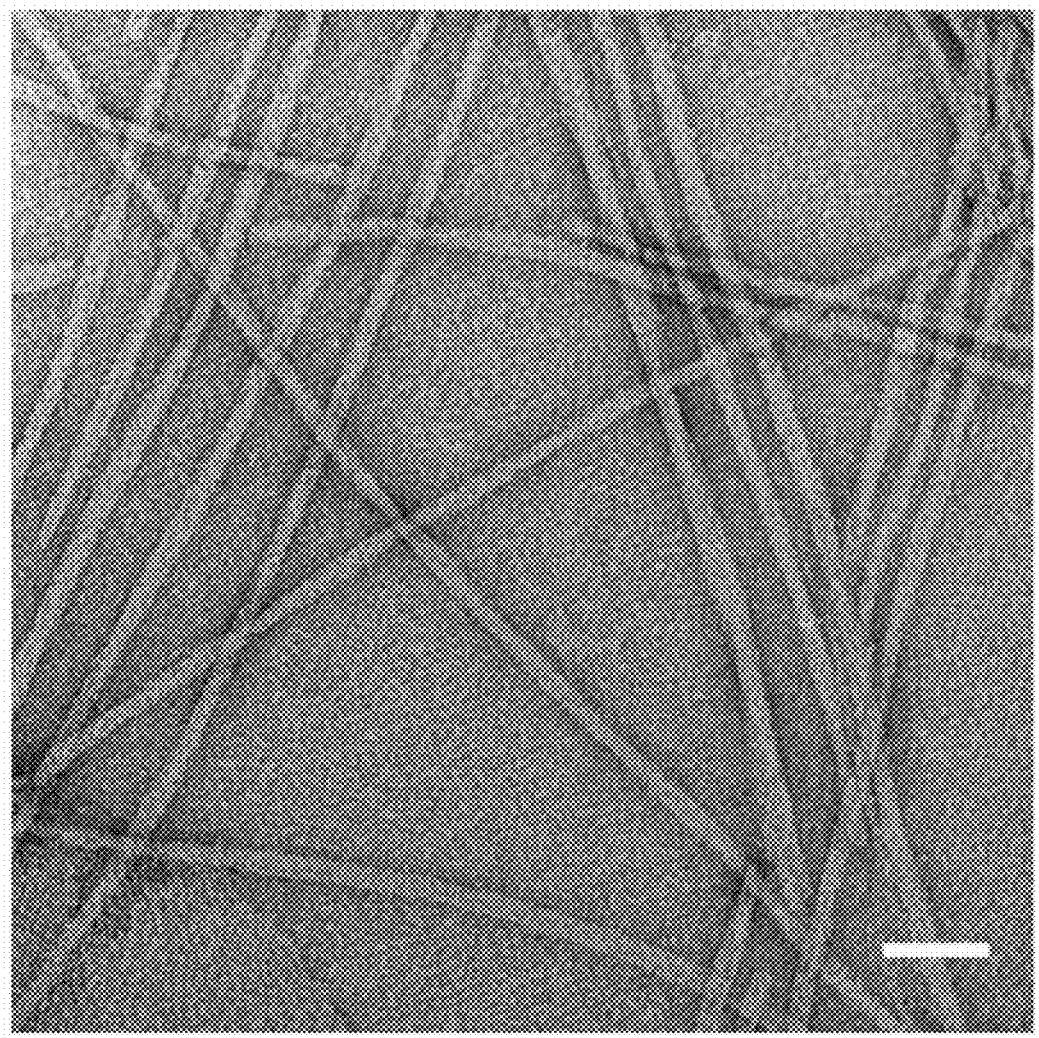
FIG. 12 is a TEM micrograph of PA 5 depicting isolated cylindrical nanofibers of uniform diameter, formed on drying of an aqueous solution onto the TEM grid.
Figure 13:
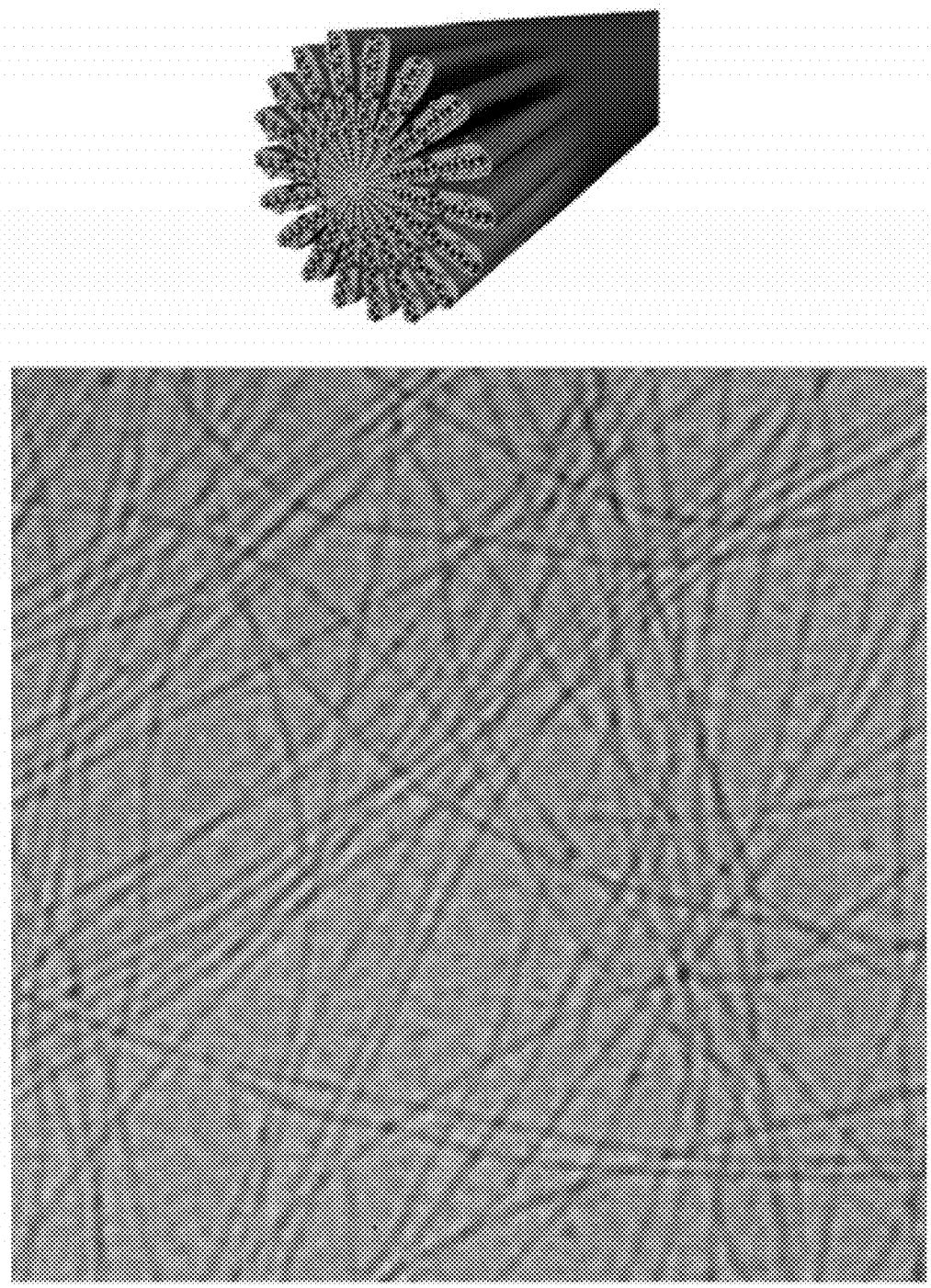
FIG. 13 depicts a schematic illustration of the peptide arrangement within the cylindrical nanofiber structure, along with a cryoTEM micrograph of PA 5 in 150 mM NaCl and 3 mM KCl, with added 5 mM $CaCl_2$.

When a 1 wt % solution of PA 5 was drop-cast and dried onto a TEM grid, cylindrical nanofibers with an average diameter of 10.8±1.5 nm were the only structures observed (FIG. 12). This diameter corresponds to 88% of twice the simulated extended length of the molecule. The change in supramolecular structure is likely the result of an increase in concentration of PA and salts during the drying process involved in the preparation of the TEM grid. This observation suggests that assembly of 5 into cylindrical nanostructures can occur when the charge on the four glutamic acids are properly screened. Indeed, when 5 mM of divalent $CaCl_2$ was added to the isotonic salt solution, cryoTEM revealed the existence of the cylindrical structures having a diameter of 9.9±1.1 nm (FIG. 13). Furthermore, the CD spectrum became positive at 210 nm, indicating the presence of β-sheet structure (FIG. 10). A weak β-sheet peak at 4.7 Å was also observed in the WAXS spectrum (FIG. 11). The addition of calcium is physiologically relevant as the cerebrospinal fluid of the nervous system contains ~1 mM of $Ca^{2+}$. No significant change in morphology was observed in the SAXS data or cryoTEM for PAs 2-4 when 5 mM $CaCl_2$ was added to the isotonic salt solution, indicating that calcium-induced self-assembly of isolated cylindrical nanofibers is inhibited by the presence of interdigitated IKVAV beta-sheets in these compounds.

Example 9

Neuronal Cell Culture

P19 embryonal carcinoma cells were cultured in media composed of α-MEM (Gibco), 7.5% newborn calf serum (Lonza), 2.5% fetal bovine serum (Gibco), penicillin (100 units/ml) and streptomycin (100 ug/ml) (Invitrogen). Neuronal differentiation was induced by plating P19 cells in non-treated Petri dishes in media containing 5 uM retinoic acid (Sigma) for 4 days. Neurospheres were collected from the Petri dish and allowed to settle in a centrifuge tube for 10 minutes. Media was removed, then trypsin/EDTA solution was added and the tube was gently agitated for 5 minutes. Cells were dissociated by triturating the neurospheres, then media was added to inactivate the trypsin. Cells were centrifuged and the pellet resuspended in media to a concentration of 25,000 cells/ul. Cells were mixed (1:4) with PA solution. The PA/cell solution was pipetted into coverslip-bottom culture dishes (MatTek) and covered with gelling solution (150 mM NaCl, 3 mM KCl, 25 mM $CaCl_2$) for 1 minute to induce gelation, then rinsed with a 150 mM NaCl, 3 mM KCl solution, then media was added to the dish. Cells were cultured for 2 days.

In order to assay neurite outgrowth, gels were rinsed with PBS, then fixed in 4% paraformaldehyde for 30 minutes at room temperature. Gels were rinsed 3× with PBS followed by addition of 10% normal goat serum blocking solution (Invitrogen) with 0.1% Triton X-100 added. Gels were incubated overnight with primary antibody (rabbit anti-β-III-tubulin IgG, 1/2000, Covance) in blocking solution. Gels were rinsed 3× with PBS, then blocked for 30 minutes with blocking solution. Next, gels were incubated with secondary antibody (Alexa Fluor 488 goat anti-rabbit IgG, 1/100, Invitrogen) in blocking solution for 1 hour. After one PBS rinse, nuclei were stained with a 5 ug/ml solution of Hoecsht 34580 (Invitrogen) in PBS for 15 minutes, then rinsed 4 times. Gels were imaged on a Zeiss LSM 510 META laser scanning confocal microscope, individually acquiring z-stacks of randomly chosen cells with neurites. Two gels were imaged per condition for each experiment. Experiments were done in triplicate. For each condition, at least 50 neurons with neurites were imaged. Using the Simple Neurite Tracer plug-in for ImageJ software, neurites were traced and measured. A one-way ANOVA, followed by paired t-tests, were performed to determine significance between conditions. Researchers were blinded to the conditions during imaging and tracing.

Example 10

Figure 14:
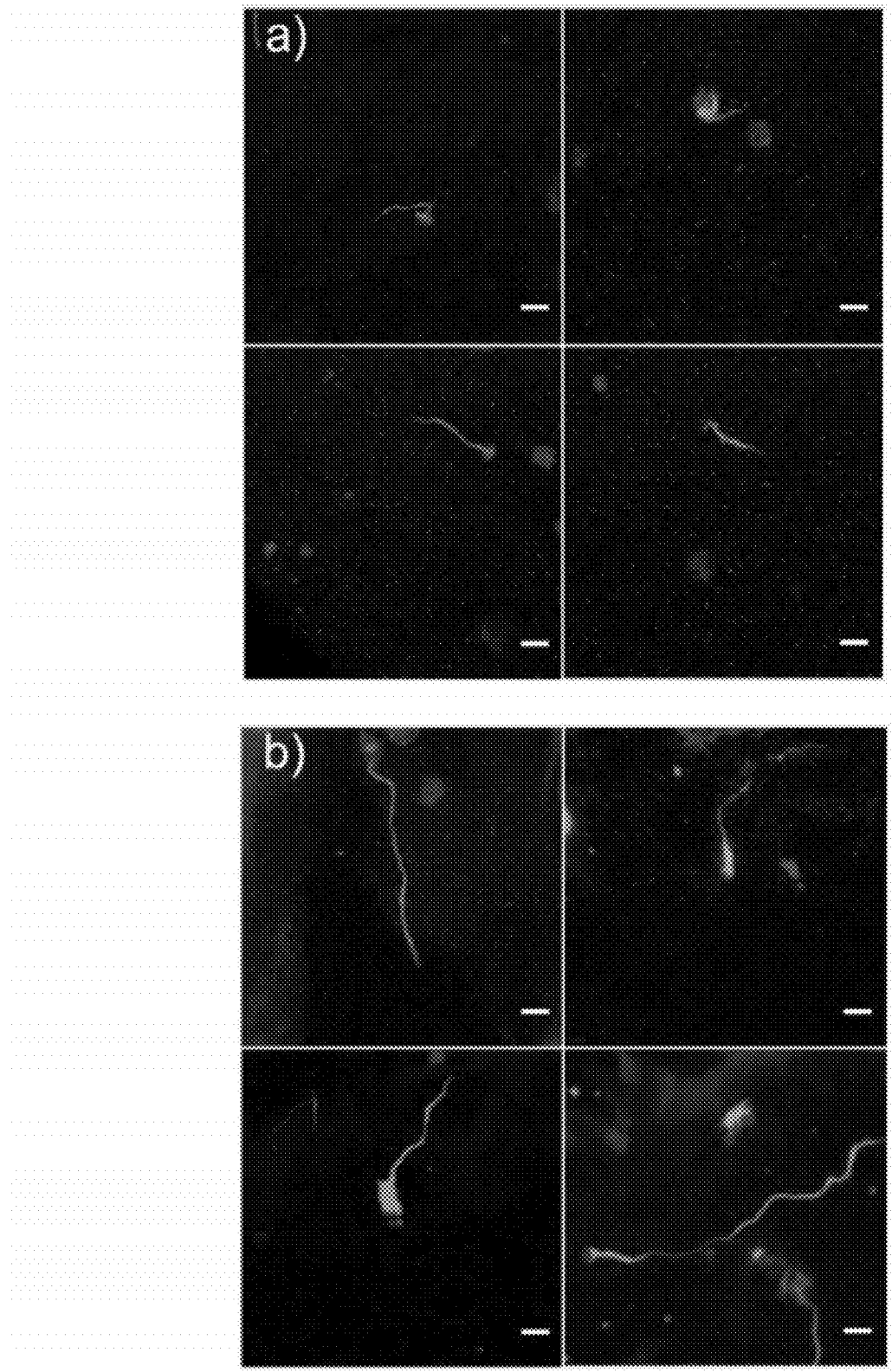
FIG. 14 depicts flattened-stack confocal fluorescence images of four randomly selected neurons cultured in peptide amphiphile gels containing 0.8 wt % of PA 1 with (a) 0.2 wt % PA 2, comprised of interdigitated trimer bundles, and (b) 0.2 wt % PA 5, comprised of individual cylindrical micelles. The scale bar represents 20 microns.

Comparison of Neurite Outgrowth in Interdigitated Beta-Sheet Nanofiber Gels and Isolated Cylindrical Nanofibers Gels The ability of gels composed of networks of filamentous structures of PAs 1-5 to promote neurite outgrowth was assessed as described in Example 9. Pluripotent murine P19 embryonal carcinoma cells were differentiated into neurons. These neurons were then homogeneously distributed into isotonic salt solutions composed of 0.8 wt % PA 1 mixed with 0.2 wt % 2-5 and gelled with 25 mM $CaCl_2$ (FIG. 3a,b). Mixtures of 1 with 2-5 were used in biological experiments in order to form robust gel matrices capable of supporting cells in culture. After two days of culture, the cells were fixed and the neurites and nuclei were fluorescently labelled green and blue using β-III-tubulin immunostaining and Hoechst staining, respectively, then imaged by confocal microscopy (FIG. 14). Neurites were traced and measured, and average neurite lengths were calculated (FIG. 15). Surprisingly, there was no enhancement of neurite outgrowth observed when neurons were cultured in gels containing PA 2 (as compared to gels of PA 1), despite the fact that it contains the neurite sprouting peptide epitope IKVAV. However, in networks formed by PAs with three or more glutamic acid residues in the charged peptide segment of the compound, neurite outgrowth was significantly increased. Cells cultured in gels containing 0.2 wt % of PA 3 and PA 5 had a 42±13% and 88±13% increase in neurite outgrowth, respectively.

These data demonstrate that surface display of the IKVAV sequence in supramolecular filaments is critical for strong bioactivity. IKVAV-bearing nanostructures that were less likely to form interdigitated bundles of cylindrical fibers (3, 5) promoted neurite outgrowth, while those that formed interdigitated bundled (2, 4) did not. Less bundling of fibers and thus less masking of the IKVAV epitopes from cellular receptors leads to higher effective concentration of IKVAV epitopes available for binding.

To test if the concentration of the IKVAV epitope affected neurite outgrowth, gels containing half the concentration (0.1 wt %) of 5 were also assayed, resulting in an increase in neurite length of 57±14%, slightly more than half the effect in gels with 0.2 wt % 5 (FIG. 15). This dose-response behavior is consistent with the hypothesis that the enhancement of neurite outgrowth is due to the favorable surface presentation and bioavailability of the IKVAV epitope on nanofibers of PA 5. By forming less aggregated, cylindrical nanostructures, PA 5, and to a lesser degree PA 3, present higher effective concentrations of bioactive IKVAV epitopes that are capable of interacting with target receptors.

To consider if surface area determines the concentration of IKVAV available for binding, it was estimated that dimer and trimer bundles to have 63% and 52% of the surface area per unit length compared to isolated nanofibers, based on the calculation described in Example 6. That 0.1 wt % of PA 5 produces a significant enhancement in neurite outgrowth, whereas 0.2 wt % PA 2 and PA 4 did not suggests that the IKVAV segment in PA 5 is also more effective at binding to receptors, even when surface area is taken into account. Since PA 4, which has the same molecular length as 5, did not show any biological activity with respect to neurite outgrowth, the enhanced coulombic repulsion due to the additional Glu residue in 5 appears to be essential to prevent inter- and intra-fiber beta-sheet formation between neighboring IKVAV epitopes, fostering an enhanced interaction with the target cellular receptor.

INDUSTRIAL APPLICABILITY

The peptide amphiphile (PA) compositions described herein possess unexpectedly superior properties to previously reported IKVAV-bearing PAs, for example increased solubility and reduced nanofiber bundling, in salt solutions similar to the extracellular environment of the central nervous system. Previously reported PA nanostructures that display the hydrophobic epitope IKVAV on their surfaces have a high propensity to interdigitate into bundles. This bundling reduces the bioactivity of the epitope toward cells encapsulated within the self-assembling PA gels. In the present invention, PA nanofiber structures are reported that suppress bundling using electrostatic forces, through the addition of appropriately placed ionizable residues. This approach will facilitate use of these peptide amphiphiles in pharmaceutical applications, for example for in vivo administration to human patients, by increasing biological activity of the compositions toward neurite outgrowth and nerve regeneration.

REFERENCES

Adams, D. N. et al. Growth cones turn and migrate up an immobilized gradient of the laminin IKVAV peptide. Journal of Neurobiology 62, 134-147, doi:10.1002/neu.20075 (2005).

Agheli, H., Malmstrom, J., Larsson, E. M., Textor, M. & Sutherland, D. S. Large area protein nanopatterning for biological applications. Nano Letters 6, 1165-1171, doi: 10.1021/nl060403i (2006).

Agius, E., Sagot, Y., Duprat, A. M. & Cochard, P. Antibodies directed against the beta 1-integrin subunit and peptides containing the IKVAV sequence of laminin perturb neurite outgrowth of peripheral neurons on immature spinal cord substrata. Neuroscience 71, 773-786, doi:0306-4522(95) 00447-5 [pii] (1996).

Bellamkonda, R., Ranieri, J. P. & Aebischer, P. LAMININ OLIGOPEPTIDE DERIVATIZED AGAROSE GELS ALLOW 3-DIMENSIONAL NEURITE EXTENSION IN-VITRO. J Neurosci Res 41, 501-509 (1995).

Berat, R. et al. Peptide-presenting two-dimensional protein matrix on supported lipid bilayers: An efficient platform for cell adhesion. Biointerphases 2, 165-172, doi:10.1116/ 1.2821954 (2007).

Chalazonitis, A., Tennyson, V. M., Kibbey, M. C., Rothman, T. P. & Gershon, M. D. The alpha1 subunit of laminin-1 promotes the development of neurons by interacting with LBP110 expressed by neural crest-derived cells immunoselected from the fetal mouse gut. J Neurobiol 33, 118-138, doi:10.1002/(SICI)1097-4695(199708)33:2<118:: AID-NEU2>3.0.CO; 2-5 [pii] (1997).

Chang, J. C., Brewer, G. J. & Wheeler, B. C. Modulation of neural network activity by patterning. Biosens Bioelectron 16, 527-533, doi:S095656630100166X [pii] (2001).

Cornish, T., Branch, D. W., Wheeler, B. C. & Campanelli, J. T. Microcontact printing: a versatile technique for the study of synaptogenic molecules. Mol Cell Neurosci 20, 140-153, doi:10.1006/mcne.2002.1101 S1044743102911012 [pii] (2002).

Cui, F. Z. et al. Cerebrum repair with PHPMA hydrogel immobilized with neurite-promoting peptides in traumatic brain injury of adult rat model. Journal of Bioactive and Compatible Polymers 18, 413-432, doi:10.1177/0883911503040470 (2003).

Duque, L., Menges, B., Borros, S. & Forch, R. Immobilization of Biomolecules to Plasma Polymerized Pentafluorophenyl Methacrylate. Biomacromolecules 11, 2818-2823, doi:10.1021/bm100910q (2010).

Ehteshami, G. R., Massia, S. & Ieee. Immobilization of bioactive peptides on Benzoeyclobutene (BCB) surface grafted-dextran for neural implant applications. Proceedings of the 25th Annual International Conference of the Ieee Engineering in Medicine and Biology Society, Vols 1-4 25, 2180-2181 (2003).

Freitas, V. M. et al. SIKVAV, a laminin alpha 1-derived peptide, interacts with: Integrins and increases protease activity of a human salivary gland adenoid cystic carcinoma cell, line through the ERK 1/2 signaling pathway. American Journal of Pathology 171, 124-138, doi:10.2353/ajpath.2007.051264 (2007).

Gunn, J. W., Turner, S. D. & Mann, B. K. Adhesive and mechanical properties of hydrogels influence neurite extension. Journal of Biomedical Materials Research Part A 72A, 91-97, doi:10.1002/jbm.a.30203 (2005).

Heller, D. A. et al. Patterned networks of mouse hippocampal neurons on peptide-coated gold surfaces. Biomaterials 26, 883-889, doi:10.1016/j.biomaterials.2004.03.029 (2005).

Hynd, M. R., Frampton, J. P., Dowell-Mesfin, N., Turner, J. N. & Shain, W. Directed cell growth on protein-functionalized hydrogel surfaces. Journal of Neuroscience Methods 162, 255-263, doi:10.1016/j.jneumeth.2007.01.024 (2007).

Itoh, S. et al. Development of a nerve scaffold using a tendon chitosan tube. Artificial Organs 27, 1079-1088 (2003).

Jung, H. J. et al. Selective and Direct Immobilization of Cysteinyl Biomolecules by Electrochemical Cleavage of Azo Linkage. Langmuir 26, 15087-15091, doi:10.1021/la102489k (2010).

Jung, J. P. et al. Co-assembling peptides as defined matrices for endothelial cells. Biomaterials 30, 2400-2410, doi:10.1016/j.biomaterials.2009.01.033 (2009).

Kam, L., Shain, W., Turner, J. N. & Bizios, R. Axonal outgrowth of hippocampal neurons on micro-scale networks of polylysine-conjugated laminin. Biomaterials 22, 1049-1054, doi:S0142961200003525 [pii] (2001).

Kasai, S. et al. Identification of multiple amyloidogenic sequences in laminin-1. Biochemistry 46, 3966-3974, doi:10.1021/bi062097t (2007).

Kibbey, M. C., Johnson, B., Petryshyn, R., Jucker, M. & Kleinman, H. K. A 110-KD NUCLEAR SHUTTLING PROTEIN, NUCLEOLIN, BINDS TO THE NEURITE-PROMOTING IKVAV SITE OF LAMININ-1. J Neurosci Res 42, 314-322 (1995).

Kibbey, M. C. et al. BETA-AMYLOID PRECURSOR PROTEIN BINDS TO THE NEURITE-PROMOTING IKVAV SITE OF LAMININ. Proceedings of the National Academy of Sciences of the United States of America 90, 10150-10153 (1993).

Kumada, Y., Hammond, N. A. & Zhang, S. G. Functionalized scaffolds of shorter self-assembling peptides containing MMP-2 cleavable motif promote fibroblast proliferation and significantly accelerate 3-D cell migration independent of scaffold stiffness. Soft Matter 6, 5073-5079, doi:10.1039/c0sm00333f (2010).

Lauer, L., Vogt, A., Yeung, C. K., Knoll, W. & Offenhausser, A. Electrophysiological recordings of patterned rat brain stem slice neurons. Biomaterials 23, 3123-3130 (2002).

Li, Q. Q. & Chau, Y. Neural differentiation directed by self-assembling peptide scaffolds presenting laminin-derived epitopes. Journal of Biomedical Materials Research Part A 94A, 688-699, doi:10.1002/jbm.a.32707 (2010).

Luckenbilledds, L., Kaiser, C. A., Rodgers, T. R. & Powell, D. D. LOCALIZATION OF THE 110-KDA RECEPTOR FOR LAMININ IN BRAINS OF EMBRYONIC AND POSTNATAL MICE. Cell and Tissue Research 279, 371-377 (1995).

Massia, S. P., Holecko, M. M. & Ehteshami, G. R. In vitro assessment of bioactive coatings for neural implant applications. Journal of Biomedical Materials Research Part A 68A, 177-186, doi:10.1002/jbm.a.20009 (2004).

Matsuzawa, M., Weight, F. F., Potember, R. S. & Liesi, P. Directional neurite outgrowth and axonal differentiation of embryonic hippocampal neurons are promoted by a neurite outgrowth domain of the B2-chain of laminin. Int J Dev Neurosci 14, 283-295, doi:0736-5748(96)00014-7 [pii] (1996).

Nakamura, M., Mie, M., Mihara, H. & Kobatake, E. Construction of a Multi-Functional Extracellular Matrix Protein That Increases Number of N1E-115 Neuroblast Cells Having Neurites. Journal of Biomedical Materials Research Part B-Applied Biomaterials 91B, 425-432, doi:10.1002/jbm.b.31418 (2009).

Niece, K. L. et al. Modification of gelation kinetics in bioactive peptide amphiphiles. Biomaterials 29, 4501-4509, doi:10.1016/j.biomaterials.2008.07.049 (2008).

Nomizu, M. Identification of biologically active sites in laminin an extracellular matrix protein. Yakugaku Zasshi-Journal of the Pharmaceutical Society of Japan 118, 566-580 (1998).

Nomizu, M. et al. IDENTIFICATION OF CELL-BINDING SITES IN THE LAMININ ALPHA-1 CHAIN CARBOXYL-TERMINAL GLOBULAR DOMAIN BY SYSTEMATIC SCREENING OF SYNTHETIC PEPTIDES. Journal of Biological Chemistry 270, 20583-20590 (1995).

Nomizu, M. et al. Cell binding sequences in mouse laminin alpha 1 chain. Journal of Biological Chemistry 273, 32491-32499 (1998).

Nomizu, M. et al. THE ALL-D-CONFIGURATION SEGMENT CONTAINING THE IKVAV SEQUENCE OF LAMININ A-CHAIN HAS SIMILAR ACTIVITIES TO THE ALL-L-PEPTIDE INVITRO AND INVIVO. Journal of Biological Chemistry 267, 14118-14121 (1992).

Nomizu, M. et al. STRUCTURE-ACTIVITY STUDY OF A LAMININ ALPHA-1 CHAIN ACTIVE PEPTIDE SEGMENT ILE-LYS-VAL-ALA-VAL (IKVAV). Febs Letters 365, 227-231 (1995).

Ohga, Y. et al. Design and activity of multifunctional fibrils using receptor-specific small peptides. Biomaterials 30, 6731-6738, doi:10.1016/j.biomaterials.2009.08.044 (2009).

Patel, N. et al. Spatially controlled cell engineering on biodegradable polymer surfaces. Faseb Journal 12, 1447-1454 (1998).

Powell, S. K. et al. Neural cell response to multiple novel sites on laminin-1 J Neurosci Res 61, 302-312, doi:10.1002/1097-4547(20000801)61:3<302::AID-JNR8>3.0.CO;2-G [pii] (2000).

Ranieri, J. P. et al. SPATIAL CONTROL OF NEURONAL CELL ATTACHMENT AND DIFFERENTIATION ON COVALENTLY PATTERNED LAMININ OLIGOPEPTIDE SUBSTRATES. International Journal of Developmental Neuroscience 12, 725-735 (1994).

Ranieri, J. P. et al. NEURONAL CELL ATTACHMENT TO FLUORINATED ETHYLENE-PROPYLENE FILMS WITH COVALENTLY IMMOBILIZED LAMININ OLIGOPEPTIDES YIGSR AND IKVAV 0.2. Journal of Biomedical Materials Research 29, 779-785 (1995).

Richard, B. L., Nomizu, M., Yamada, Y. & Kleinman, H. K. Identification of synthetic peptides derived from laminin alpha 1 and alpha 2 chains with cell type specificity for neurite outgrowth. Experimental Cell Research 228, 98-105 (1996).

Saha, K., Irwin, E. F., Kozhukh, J., Schaffer, D. V. & Healy, K. E. Biomimetic interfacial interpenetrating polymer networks control neural stem cell behavior. J Biomed Mater Res A 81, 240-249, doi:10.1002/jbm.a.30986 (2007).

Saneinejad, S. & Shoichet, M. S. Patterned glass surfaces direct cell adhesion and process outgrowth of primary neurons of the central nervous system. Journal of Biomedical Materials Research 42, 13-19 (1998).

Santiago, L. Y., Nowak, R. W., Rubin, J. P. & Marra, K. G. Peptide-surface modification of poly(caprolactone) with laminin-derived sequences for adipose-derived stem cell applications. Biomaterials 27, 2962-2969, doi:10.1016/j.biomaterials.2006.01.011 (2006).

Shaw, D. & Shoichet, M. S. Toward spinal cord injury repair strategies: Peptide surface modification of expanded poly (tetrafluoroethylene) fibers for guided neurite outgrowth in vitro. Journal of Craniofacial Surgery 14, 308-316 (2003).

Silva, G. A. et al. Selective differentiation of neural progenitor cells by high-epitope density nanofibers. Science 303, 1352-1355, doi:Doi 10.1126/Science.1093783 (2004).

Song, Y. L., Zheng, Q. X., Wu, Y. C. & Guo, X. D. Two-dimensional Effects of Hydrogel Self-organized from IKVAV-containing Peptides on Growth and Differentiation of NSCs. Journal of Wuhan University of Technology-Materials Science Edition 24, 186-192, doi:10.1007/s11595-009-2186-1 (2009).

Suzuki, M. et al. Tendon chitosan tubes covalently coupled with synthesized laminin peptides facilitate nerve regeneration in vivo. J Neurosci Res 72, 646-659, doi:10.1002/jnr.10589 (2003).

Svedhem, S. et al. In situ peptide-modified supported lipid bilayers for controlled cell attachment. Langmuir 19, 6730-6736, doi:10.1021/la034172w (2003).

Takagi, Y. et al. Conserved neuron promoting activity in *Drosophila* and vertebrate laminin alpha 1. Journal of Biological Chemistry 271, 18074-18081 (1996).

Tashiro, K. et al. A SYNTHETIC PEPTIDE DEDUCED FROM THE SEQUENCE IN THE CROSS-REGION OF LAMININ-A CHAIN MEDIATES NEURITE OUTGROWTH, CELL ATTACHMENT AND HEPARIN-BINDING. Biochemical Journal 302, 73-79 (1994).

Tashiro, K. et al. A SYNTHETIC PEPTIDE CONTAINING THE IKVAV SEQUENCE FROM THE A-CHAIN OF LAMININ MEDIATES CELL ATTACHMENT, MIGRATION, AND NEURITE OUTGROWTH. Journal of Biological Chemistry 264, 16174-16182 (1989).

Tong, Y. W. & Shoichet, M. S. Enhancing the neuronal interaction on fluoropolymer surfaces with mixed peptides or spacer group linkers. Biomaterials 22, 1029-1034 (2001).

Tysseling, V. M. et al. Self-Assembling Peptide Amphiphile Promotes Plasticity of Serotonergic Fibers Following Spinal Cord Injury. J Neurosci Res 88, 3161-3170, doi:Doi10.1002/Jnr.22472 (2010).

Tysseling-Mattiace, V. M. et al. Self-assembling nanofibers inhibit glial scar formation and promote axon elongation after spinal cord injury. J Neurosci 28, 3814-3823, doi:Doi 10.1523/Jneurosci.0143-08.2008 (2008).

Wheeler, B. C., Corey, J. M., Brewer, G. J. & Branch, D. W. Microcontact printing for precise control of nerve cell growth in culture. J Biomech Eng 121, 73-78 (1999).

Yamada, M. et al. Ile-Lys-Val-Ala-Val (IKVAV)-containing laminin alpha 1 chain peptides form amyloid-like fibrils. Febs Letters 530, 48-52 (2002).

Yeung, C. K., Lauer, L., Offenhausser, A. & Knoll, W. Modulation of the growth and guidance of rat brain stem neurons using patterned extracellular matrix proteins. Neurosci Lett 301, 147-150, doi:S0304394001016287 [pii] (2001).

Yoshida, I. et al. Identification of a heparin binding site and the biological activities of the laminin alpha 1 chain carboxy-terminal globular domain. Journal of Cellular Physiology 179, 18-28 (1999).

Zhang, Z. X., Zheng, Q. X., Wu, Y. C. & Hao, D. J. Compatibility of Neural Stem Cells with Functionalized Self-assembling Peptide Scaffold In vitro. Biotechnology and Bioprocess Engineering 15, 545-551, doi:10.1007/s12257-009-3076-2 (2010).

Zou, Z. W., Zheng, Q. X., Wu, Y. C., Song, W. & Wu, B. Growth of rat dorsal root ganglion neurons on a novel self-assembling scaffold containing IKVAV sequence. Materials Science & Engineering C-Materials for Biological Applications 29, 2099-2103, doi:10.1016/j.msec.2009.04.009 (2009).

Zustiak, S. P., Durbal, R. & Leach, J. B. Influence of cell-adhesive peptide ligands on poly(ethylene glycol) hydrogel physical, mechanical and transport properties. Acta Biomaterialia 6, 3404-3414, doi:10.1016/j.actbio.2010.03.040 (2010).

All patents and publications mentioned herein are incorporated by reference in their entirety. Nothing herein is to be construed as an admission that the invention is not entitled to antedate such disclosure by virtue of prior invention.

While the invention has been described in detail and with reference to specific embodiments thereof, it is to be understood that the foregoing description is exemplary and explanatory in nature and is intended to illustrate the invention and its preferred embodiments. Through routine experimentation, one skilled in the art will readily recognize that various changes and modifications can be made therein without departing from the spirit and scope of the invention. For instance, various peptide amphiphiles have been described in conjunction with specific amino acid residues; however, other residues can be used herewith to promote a particular tissue growth and regeneration on the nanostructures prepared therefrom. Likewise, while the present invention has been described as applicable to biomedical or tissue engineering use, other advantages and features will become apparent from the claims filed hereafter, with the scope of such claims to be determined by their reasonable equivalents, as would be understood by those skilled in the art.

We claim:

1. A peptide amphiphile compound self-assembled into a nanostructure, said peptide amphiphile compound comprising an acyl group of six or more carbons, and a peptide segment comprising VVAA(E)$_x$G (SEQ ID NOS: 16-19), wherein x is 3 to 6.

2. The compound of claim 1 wherein the peptide segment comprises VVAA(E)$_x$G (SEQ ID NOS: 16-17), wherein x is 3 to 4.

3. The compound of claim 1 further comprising the amino acid sequence IKVAV (SEQ ID NO: 1).

4. The compound of claim 1, wherein the acyl group comprises a palmitoyl group.

5. A composition comprising:
   a) a first peptide amphiphile comprising the compound of claim 1; and
   b) a second peptide amphiphile comprising the peptide sequence (V)x(A)y(E)z-NH$_2$, wherein x=y=z=2.

* * * * *

SEQUENCE LISTING

<160> NUMBER OF SEQ ID NOS: 19

<210> SEQ ID NO 1
<211> LENGTH: 5
<212> TYPE: PRT
<213> ORGANISM: Artificial Sequence
<220> FEATURE:
<223> OTHER INFORMATION: Synthetic

<400> SEQUENCE: 1

Ile Lys Val Ala Val
1               5

<210> SEQ ID NO 2
<211> LENGTH: 4
<212> TYPE: PRT
<213> ORGANISM: Artificial Sequence
<220> FEATURE:
<223> OTHER INFORMATION: Synthetic

<400> SEQUENCE: 2

Val Val Ala Ala
1

<210> SEQ ID NO 3
<211> LENGTH: 6
<212> TYPE: PRT
<213> ORGANISM: Artificial Sequence
<220> FEATURE:
<223> OTHER INFORMATION: Synthetic

<400> SEQUENCE: 3

Val Val Ala Ala Glu Glu
1               5

<210> SEQ ID NO 4
<211> LENGTH: 12
<212> TYPE: PRT
<213> ORGANISM: Artificial Sequence
<220> FEATURE:
<223> OTHER INFORMATION: Synthetic

<400> SEQUENCE: 4

Val Val Ala Ala Glu Glu Gly Ile Lys Val Ala Val
1               5                   10

<210> SEQ ID NO 5
<211> LENGTH: 13
<212> TYPE: PRT
<213> ORGANISM: Artificial Sequence
<220> FEATURE:
<223> OTHER INFORMATION: Synthetic

<400> SEQUENCE: 5

Val Val Ala Ala Glu Glu Glu Gly Ile Lys Val Ala Val
1               5                   10

<210> SEQ ID NO 6
<211> LENGTH: 14
<212> TYPE: PRT
<213> ORGANISM: Artificial Sequence
<220> FEATURE:
<223> OTHER INFORMATION: Synthetic

<400> SEQUENCE: 6

Val Val Ala Ala Glu Glu Glu Gly Gly Ile Lys Val Ala Val

-continued

```
<210> SEQ ID NO 7
<211> LENGTH: 14
<212> TYPE: PRT
<213> ORGANISM: Artificial Sequence
<220> FEATURE:
<223> OTHER INFORMATION: Synthetic

<400> SEQUENCE: 7

Val Val Ala Ala Glu Glu Glu Glu Gly Ile Lys Val Ala Val
1               5                   10

<210> SEQ ID NO 8
<211> LENGTH: 5
<212> TYPE: PRT
<213> ORGANISM: Artificial Sequence
<220> FEATURE:
<223> OTHER INFORMATION: Synthetic

<400> SEQUENCE: 8

Val Ala Val Lys Ile
1               5

<210> SEQ ID NO 9
<211> LENGTH: 5
<212> TYPE: PRT
<213> ORGANISM: Artificial Sequence
<220> FEATURE:
<223> OTHER INFORMATION: Synthetic

<400> SEQUENCE: 9

Val Ala Val Lys Ile
1               5

<210> SEQ ID NO 10
<211> LENGTH: 5
<212> TYPE: PRT
<213> ORGANISM: Artificial Sequence
<220> FEATURE:
<223> OTHER INFORMATION: Synthetic

<400> SEQUENCE: 10

Val Val Ile Ala Lys
1               5

<210> SEQ ID NO 11
<211> LENGTH: 16
<212> TYPE: PRT
<213> ORGANISM: Artificial Sequence
<220> FEATURE:
<223> OTHER INFORMATION: Synthetic

<400> SEQUENCE: 11

Cys Arg Lys Gln Ala Ala Ser Ile Lys Val Ala Val Ser Ala Asp Arg
1               5                   10                  15

<210> SEQ ID NO 12
<211> LENGTH: 3
<212> TYPE: PRT
<213> ORGANISM: Artificial Sequence
<220> FEATURE:
<223> OTHER INFORMATION: Synthetic

<400> SEQUENCE: 12

Glu Glu Gly
1
```

```
<210> SEQ ID NO 13
<211> LENGTH: 4
<212> TYPE: PRT
<213> ORGANISM: Artificial Sequence
<220> FEATURE:
<223> OTHER INFORMATION: Synthetic

<400> SEQUENCE: 13

Glu Glu Glu Gly
1

<210> SEQ ID NO 14
<211> LENGTH: 5
<212> TYPE: PRT
<213> ORGANISM: Artificial Sequence
<220> FEATURE:
<223> OTHER INFORMATION: Synthetic

<400> SEQUENCE: 14

Glu Glu Glu Gly Gly
1               5

<210> SEQ ID NO 15
<211> LENGTH: 5
<212> TYPE: PRT
<213> ORGANISM: Artificial Sequence
<220> FEATURE:
<223> OTHER INFORMATION: Synthetic

<400> SEQUENCE: 15

Glu Glu Glu Glu Gly
1               5

<210> SEQ ID NO 16
<211> LENGTH: 8
<212> TYPE: PRT
<213> ORGANISM: Artificial Sequence
<220> FEATURE:
<223> OTHER INFORMATION: Synthetic

<400> SEQUENCE: 16

Val Val Ala Ala Glu Glu Glu Gly
1               5

<210> SEQ ID NO 17
<211> LENGTH: 9
<212> TYPE: PRT
<213> ORGANISM: Artificial Sequence
<220> FEATURE:
<223> OTHER INFORMATION: Synthetic

<400> SEQUENCE: 17

Val Val Ala Ala Glu Glu Glu Glu Gly
1               5

<210> SEQ ID NO 18
<211> LENGTH: 10
<212> TYPE: PRT
<213> ORGANISM: Artificial Sequence
<220> FEATURE:
<223> OTHER INFORMATION: Synthetic

<400> SEQUENCE: 18

Val Val Ala Ala Glu Glu Glu Glu Glu Gly
1               5                   10

<210> SEQ ID NO 19
```

```
<211> LENGTH: 11
<212> TYPE: PRT
<213> ORGANISM: Artificial Sequence
<220> FEATURE:
<223> OTHER INFORMATION: Synthetic

<400> SEQUENCE: 19

Val Val Ala Ala Glu Glu Glu Glu Glu Glu Gly
1               5                   10
```